(12) United States Patent
Wang et al.

(10) Patent No.: US 12,158,457 B2
(45) Date of Patent: Dec. 3, 2024

(54) GAS-SENSITIVE-GAS-CHROMATOGRAPHIC ELECTRONIC NOSE INSTRUMENT AND ONLINE ANALYSIS METHOD OF MULTIPLE STATE PARAMETERS OF FERMENTATION AND MALODOROUS POLLUTANT PROCESSES

(71) Applicant: East China University of Science and Technology, Shanghai (CN)

(72) Inventors: Zejian Wang, Shanghai (CN); Daqi Gao, Shanghai (CN); Xiaoqin Zhang, Shanghai (CN); Bo Li, Shanghai (CN); Fang Cai, Shanghai (CN); Jianhua Li, Shanghai (CN); Mingjian Cheng, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 265 days.

(21) Appl. No.: 17/794,767

(22) PCT Filed: Jul. 18, 2020

(86) PCT No.: PCT/CN2020/102885
§ 371 (c)(1),
(2) Date: Jul. 22, 2022

(87) PCT Pub. No.: WO2021/147274
PCT Pub. Date: Jul. 29, 2021

(65) Prior Publication Data
US 2023/0152287 A1    May 18, 2023

(30) Foreign Application Priority Data

Jan. 23, 2020   (CN) .......................... 202010077146.1
Jan. 23, 2020   (CN) .......................... 202010077147.6

(51) Int. Cl.
*G01N 30/88*    (2006.01)
*G01N 1/24*     (2006.01)
(Continued)

(52) U.S. Cl.
CPC ............... *G01N 30/88* (2013.01); *G01N 1/24* (2013.01); *G01N 33/00* (2013.01); *G06N 3/045* (2023.01)

(58) Field of Classification Search
CPC .. G01N 1/24; G01N 2030/8813; G01N 30/86; G01N 30/88; G01N 33/00; G01N 33/0047; G06N 3/045
See application file for complete search history.

(56) References Cited

U.S. PATENT DOCUMENTS 9,322,813 B2 *  4/2016  Anderson, Jr. ........ G01N 30/38
10,948,467 B2 * 3/2021  Gao ....................... G01N 33/00
(Continued)

FOREIGN PATENT DOCUMENTS

CN         1367381 A      9/2002
CN       101093217 A     12/2007
(Continued)

OTHER PUBLICATIONS

International Search Report; China National Intellectual Property Administration; Patent Application No. PCT/CN2020/102885; Oct. 29, 2020; 6 pages.
(Continued)

*Primary Examiner* — Andre J Allen
(74) *Attorney, Agent, or Firm* — Taft Stettinius & Hollister LLP

(57) ABSTRACT

A method for online detecting and analyzing multiple state parameters in fermentation and malodorous pollution processes by using an electronic nose instrument of gas sensitivity and gas chromatography, where the electronic nose
(Continued)

instrument includes a gas sensor array module, a capillary gas chromatographic column module, a gas auto-sampling module, a computer control and analysis module and an auxiliary gas source, which is configured to perform cyclically long-term online detection and intelligent analysis of a plurality of bio-fermentation processes or a plurality of malodorous pollution processes.

14 Claims, 9 Drawing Sheets

(51) Int. Cl.
  *G01N 33/00* (2006.01)
  *G06N 3/045* (2023.01)

(56) References Cited

U.S. PATENT DOCUMENTS

| | | | |
|---|---|---|---|
| 2002/0182739 A1 | 12/2002 | Sadik et al. | |
| 2023/0141978 A1* | 5/2023 | Wang | G06N 3/045 |
| | | | 73/31.07 |

FOREIGN PATENT DOCUMENTS

| | | | |
|---|---|---|---|
| CN | 20209298 U | | 12/2011 |
| CN | 202092981 U | | 12/2011 |
| CN | 103454335 A | | 12/2013 |
| CN | 103675127 A | | 3/2014 |
| CN | 104655739 A | * | 5/2015 |
| CN | 105738503 A | | 7/2016 |
| CN | 107085018 A | | 8/2017 |
| CN | 108709955 A | | 10/2018 |
| CN | 108896706 A | | 11/2018 |
| CN | 108896706 B | | 4/2019 |
| CN | 109724645 A | | 5/2019 |
| CN | 110632189 A | | 12/2019 |
| CN | 110702815 A | | 1/2020 |
| CN | 220381063 U | * | 1/2024 |
| CN | 117929604 A | * | 4/2024 |
| CN | 220819933 U | * | 4/2024 |
| EP | 1376122 A1 | | 1/2004 |
| IN | 107748165 A | | 3/2018 |

OTHER PUBLICATIONS

Written Opinion; China National Intellectual Property Administration; Patent Application No. PCT/CN2020/102885; Oct. 29, 2020; 3 pages.

First Office Action; The State Intellectual Property Office of People's Republic of China; Patent Application No. 202010077147.6; Sep. 30, 2020; 9 pages total.

First Office Action; The State Intellectual Property Office of People's Republic of China; Patent Application No. 202010077146.1; Sep. 30, 2020; 10 pages total.

Jun-Cheng Li et al.; Detection of Sulfur Containing Odorous Gas Based on Micro-Gas Chromatography Technology; Modern Chemical Industry; Dec. 2016; 4 pages.

Xu-Lan Zhao et al.; Analysis of Sulfur-Containing Odorous Gas Mixture by Capillary Gas Chromatography; Chinese Journal of Analysis Laboratory; Nov. 2015; 5 pages; vol. 34 No. 11.

* cited by examiner (a), Response curve of the gas sensor TGS826 to a petroleum wax vapor (b), Response curve of the gas sensor TGS832 to a 2,000ppm ethylene vapor (c), Response curve of the gas sensor TGS822 to a 5,000*ppm* ethanol vapor (a), Less than 10 chromatographic peaks in a specified interval (b), More than 10 chromatographic peaks in a specified interval

GAS-SENSITIVE-GAS-CHROMATOGRAPHIC ELECTRONIC NOSE INSTRUMENT AND ONLINE ANALYSIS METHOD OF MULTIPLE STATE PARAMETERS OF FERMENTATION AND MALODOROUS POLLUTANT PROCESSES

CROSS REFERENCE TO RELATED APPLICATIONS

This is a national stage application filed under 37 U.S.C. 371 based on International Patent Application No. PCT/CN2020/102885, filed on Jul. 18, 2020, which claims priority to Chinese Patent Application No. 202010077146.1, filed with the China National Intellectual Property Administration (CNIPA) on Jan. 23, 2020 and Chinese Patent Application No. 202010077147.6, filed with the China National Intellectual Property Administration (CNIPA) on Jan. 23, 2020, the disclosures of which are incorporated herein by reference in their entireties.

TECHNICAL FIELD

The present disclosure provides a method for online detecting and analyzing multiple state parameters of fermentation and malodorous pollutant processes by using an electronic nose instrument of gas sensitivity and gas chromatography, used for the requirements of multi-source online detection and multi-parameter analysis in a process represented by bio-fermentation and malodorous pollution, involving the technical fields of artificial intelligence, computer, bioengineering, environmental protection, analytical chemistry and others, and it mainly solves a series of problems of poor sensitivity of a gas sensor, poor selectivity of a gas sensor array caused by a single perception information selection method, poor linearity of a chromatography caused by a peak-to-peak complete separation method, optimized combination of the gas sensor array and a gas chromatographic column structure, multi-source perception information selection and fusion and the like, so as to achieve the aims of long-term circulation, multi-source online detection and multi-parameter online analysis of the bio-fermentation and malodorous pollution processes by the electronic nose instrument.

BACKGROUND

Olfaction simulation—Electronic nose method uses a number of overlapping gas sensor arrays to achieve rapid odor detection, and uses machine learning method to perform qualitative and quantitative odor analysis. Online odor detection and analysis has become a key application technique in the industrial fields of bioengineering, environmental protection, food and others. Special attention has been paid to an electronic nose instrument due to its good characteristics of high perception speed, non-contact detection, simple and convenient operation, etc. The present research situation on electronic nose theory and technique is that the sensitivity of a single gas sensor has already reached up to $10^{-7}$ (V/V) or 0.1 ppm order of magnitude, but its selectivity is relatively poor, and therefore the stability, linearity and qualitative and quantitative capabilities of the electronic nose instrument are not ideal. What is more serious is that an online electronic nose instrument of fermentation is still blank in the world. Under the background of great demand, the electronic nose technology is repeatedly listed in the national high technology R&D program of China (863), the national science and technology support program of China, and the national key R&D program of China.

On-line detection of multiple process parameters is the prerequisite for real-time estimation, prediction and control of bio-fermentation and malodorous pollution processes. The environmental malodorous pollution time span can be months or years; the bio-fermentation process can be as short as 1-2 days, or as long as days (such as, beer fermentation), months, or even years. The change of the state of the bio-fermentation and malodorous pollution processes is slightly exaggerated by using "instantaneous change", but the detection and analysis period in the unit of "hour" is definitely too long. The measured object does not change greatly in the state of 1 min, namely a detection period is not necessary to be less than 1 min; in turn, the bio-fermentation or malodorous pollution state may change greatly within 1 hour, and it is not suitable to consider the "online" detection as the "intermittent" detection of the regular manual sampling for 1 hour or more in the period. Accordingly, the online detection and analysis period of the electronic nose instrument for a single bio-fermentation process (fermentation tank) or a single malodorous pollution monitoring point should not be over $T_0=10$ min, and the circulation online detection and analysis period $T=n*T_0$ for multiple fermentation tanks or multiple malodorous monitoring points should be within 1 hour, therefore, judge whether a detection and analysis method is on line in this way is much more reasonable.

It is unrealistic and inconceivable to analyze fermentation process by artificial smelling of tail gas. Moreover, quantitative determination of odor concentration, food and flavor odor intensity by smell is criticized for its cumbersome process, high cost, low efficiency, poor objectivity and operability. The long-term artificial smelling of the malodorous odors can cause serious harm to the human body, and is incompatible with the desire of people to pursue a beautiful life in the age of artificial intelligence. Online multi-source detection, identification and simultaneous quantitative prediction of multiple components of complex odors are not only a complex theoretical problem, but also technical and application problems which need to be solved urgently.

One of the main development trends of the electronic nose technology is that by using multiple sensitive elements with necessary sensitivity to form an array, big data and artificial intelligence technology are emphatically utilized to improve the qualitative and quantitative capabilities, including type identification, intensity and quantitative estimation of main components of many complex odors. "Long-term continuous online detection and analysis" is a main working mode of an electronic nose instrument, and is mainly used for online qualitative analysis and prediction of concentrations of multiple main components in the process of objects such as the bio-fermentation and malodorous pollutants, and is characterized with abundant gas volume, fixed sampling period (such as, 5 min), flow rate and duration interval and repeated, and an electronic nose instrument performs qualitative and quantitative analysis by perceiving the fermentation tail gases and malodorous gases again and again.

The basic premise of the "continuous online" detection and analysis of the electronic nose instrument is that the core, namely the gas sensor array, has a remarkable perception capability on a tested object. From the perspective of application, the performance indices of the gas sensor to be achieved include: high sensitivity (ppm level or even ppb level), fast response speed (within 1 min), stable working state, high commercialization level, long service life (3-5 years), small size, and good selectivity.

According to the difference of sensitive materials and working principles, Reference [1] has listed the sensitive properties of 6 types of common-used gas elements, i.e., metal oxide semi-conductor (MOS), electrochemical (EC), conducting polymer (CP), quartz microbalance (QMB), surface acoustic wave (SAW), and photo ionization detector (PID). Compared with the MOS-type, the EC gas sensor has a better selectivity, but has a larger size, a shorter service life with at least 1 year, and a lower sensitivity with one order of magnitude or more. Compared with the MOS-type, the PID gas sensor has a large size, a narrow sensitive range, a higher price and a shorter service life with about half a year. Moreover, the EC and the PID gas sensors are only suitable for detecting the malodorous pollutants. The sensitivity of the QMB and SAW gas sensor elements is lower than that of the MOS type by 1 order of magnitude or more. Therefore, more sensitive film materials need to be developed, and the size of gas sensors needs to be further reduced. By taking various factors into consideration, the MOS gas sensors represented by $SnO_2$ are most suitable for being used as the sensitive elements of the electronic nose instrument.

It must be noted that the single-type gas sensor as well as their array made of the above 6 sensitive materials thereof have a very limited perception capability and do not meet the requirements of online processing detection for bio-fermentation, malodorous pollution and the like. Extensive experiments have indicated the following facts: (i) even the MOS element with the highest sensitivity is not sensitive enough to the precursor—phenylacetic acid during the penicillin fermentation; (ii) anyone existing electronic nose is not sensitive enough to the malodorous gas in a specified pig farm. It has been mentioned earlier that the sensitivity of current gas sensors has reached the highest order of magnitude of $10^{-7}$ (V/V), but that is only the case of a certain MOS sensor for a certain odorous components, and is not a common phenomenon. One of the most typical examples is the detection of malodorous pollutants and the prediction of the concentration indices of their main compounds by using the electronic nose instrument. The specified indices by the Chinese national standard GB14554 include 8 concentration values of $NH_3$, $H_2S$, $CS_2$, $C_3H_9N$, $CH_4S$, $C_2H_6S$, $C_2H_6S_2$ and $C_8H_8$, and an overall odor concentration or called OU (odor unit) value, all of which are referred to as (8+1) concentration control index values of malodorous pollutants for short. At present, one gas sensor array that is not only simultaneously sensitive but also has good selectivity to such 6 malodorous organic compounds as $CS_2$, $C_3H_9N$, $CH_4S$, $C_2H_6S$, $C_2H_6S_2$ and $C_8H_8$ does not exist, and is difficult to be developed out in a short term. In other words, it is difficult to realize the online detection and prediction of (8+1) malodorous pollutant index values by using one gas sensor array only made of the mentioned-above 6 gas sensitive materials.

It is impossible to use an array of redundant gas sensors to detect numerous odors. On the one hand, the structure of the electronic nose instrument will be quite complex, and on the other, the current gas sensors are insufficient in sensitivity and limited in overlapping perception range [1]. Therefore, the gas chromatography method has attracted a high degree of interest. The chromatographic electronic nose commodities have emerged, such as a Heracles II gas chromatography electronic nose produced by the α-MOS Corporation Ltd, France. In essence, the Heracles II electronic nose is used for one-time on-site detection and analysis of odor on the basis of completely separated chromatographic peaks in a single gas sampling period of $T_0$=5-8 min at any time, and is not suitable for the long-term continuous online detections.

In terms of selectivity, the gas chromatography method is good, but the MOS gas sensor method is poor. However, this difference is only relative, and the "qualitative ability" of the gas chromatography to unknown samples is still "weak". That is, in the absence of spectrums for either internal or external standard samples, the constituent and components of the unknown samples cannot be determined at all by a single measured spectrum. The second defect of the gas chromatography is that the "selectivity" of the chromatographic column is not universal. A particular chromatographic column is sensitive to a particular sample only under certain conditions, i.e. the particular chromatographic column may only detect a particular sample in a particular range. The chromatographic perception parameters of the particular sample will change while either sampling conditions or test conditions or chromatographic column parameters change.

It should be noted that the core of gas chromatography is separation but not detection. The effective method to improve the chromatographic separation include: (1) the column length is properly increased; (2) the sampling volume and the sampling time are properly reduced; (3) the flow rate of carrier gas is properly reduced; (4) the temperature of the chromatographic column is properly reduced; (5) the temperature of the vaporization chamber is properly increased. It should be made clear that the proper increase of either the temperature of the chromatographic column or the flow rate of carrier gas will be beneficial to shorten the retention time, and that the separation of chromatographic peaks and the reduction of the retention time are sometimes contradictory.

An odor is a mixture of tens, hundreds or even thousands of compounds, and all of which have a molecular weight of less than 300 Dalton. Retention time is an important qualitative analytical parameter for the gas chromatography, and the chromatographic retention time values of the 8 malodorous compounds specified by GB 14554 are mostly less than 8 min. To increase the detection speed of the gas chromatography, a capillary column with a larger inner diameter of φ0.53 mm and a column length of 30 m may be selected and thus design and manufacture the GC constant-temperature working chamber. $H_2$ is used as both carrier gas and fuel gas. The programmed temperature, the sampling of tested gases and the pushing processes of carrier gas are precisely controlled. The capillary gas chromatography column as well as the whole chromatography column module should be easily replaced and installed. In the period of $T_0 \leq 10$ min, the sampling flow rate of the tested gas may be between 1.0 and 15 ml/min, and a sampling duration may be between 0.5 s and 1.5 s. At the moment, a semi-separation multi-peak chromatogram with limited duration, say $T_0 \leq 10$ min, may be obtained.

The phenomenon of semi-separation/incomplete separation of chromatogram is a result of the combined action of many factors, including the constituent of the tested gas, the characteristics of the chromatographic column itself, the setting of working parameters of the chromatographic instrument, the performance of a detector, the length of time recorded and others. Incomplete separation or semi-separation of chromatographic peaks is a common phenomenon, and complete separation is only an ideal or extreme case. The more components in a tested object are, the more difficult the peak-to-peak complete separation is, and thus the cost is long detection time. In a period of progressive marathon race, although the winner did not produce, the win-lose trend has been scored, the winner is in "running in front of the team in the race". In the second half of a progressive marathon race, although the rankings have not been finally created, the trend of winning or losing has been formed, and the winner and the runner-up are "running in the top group of the competition team" This is a biological basis for the gas chromatography to perform an online detection and analysis by using the semi-separation chromatogram. The semi-separation chromatogram is part of the full-separation chromatogram, which is equivalent to the marathon race "running in the top group of the competition team in the marathon race". As long as the compositions of the tested samples and the test condition of the chromatographic column remain unchanged, the semi-separation chromatograms obtained by testing the same sample at different times remain unchanged, and a positional relationship between the semi-separation chromatogram and the full-separation chromatogram is also unchanged. That is to say, some main characteristics of the full-separation chromatogram may be speculated by using the semi-separation chromatogram, for example, to speculate the presence and content of some components with long retention time that do not appear in the semi-separation chromatogram. For the bio-fermentation, malodorous pollution and other process analysis, it is enough to obtain the information representing the main state parameters. The semi-separation chromatogram actually contains the main information of the full-separation chromatogram, and the key is how to obtain the required information from the chromatogram and explain it.

Either single chromatographic column or a gas sensor array with a single type of sensitive material is limited in terms of perception range. It is difficult for a gas chromatography to analyze the inorganic and the easily-decomposable high-boiling organic compounds, and also to qualitatively analyze the unknown compounds. It is not suitable for the gas chromatography to analyze some single compounds with strong polarity or complex compounds with quite different polarity, as well as some carbon-free compounds. For example, the gas chromatography using a hydrogen flame ionization detector (FID) does not effectively detect inorganic compounds. This is the driver of the present disclosure to develop a new online detection and analysis method of electronic nose instrument fusing the gas sensor array and the capillary gas chromatographic column. Why should the two, the gas sensor array and the capillary column, be fused? One of the reasons is that the present gas sensors have not only poor selectivity but also low sensitivity to some compounds. It is not possible, for instance, only for the existing gas sensor arrays to realize online quantitative prediction of some non-reduced or non-oxidized inorganic compounds, penicillin fermentation precursor-phenylacetic acid, as well as 8+1 malodorous pollution indexes specified by GB14554. The second reason is that the gas chromatography has poor online performance and a single chromatographic column is only with limited selectivity. For example, the gas chromatography is able only to detect the samples with good thermal stability. According to incomplete statistics, Agilent Technologies Co. Ltd. provides more than a thousand kind of ready-to-use chromatographic columns. The fact of "chromatographic column selection and replacement operation" itself indicates that a single chromatographic column is limited in the aspect of detection range.

A typical example is that the Chinese national standard GB14554 specifies that the concentrations of two malodorous pollutants, i.e., $NH_3$ and $CS_2$, are detected by the spectrophotometry, and the concentrations of six malodorous pollutants, i.e., $H_2S$, $C_3H_9N$, $CH_4S$, $C_2H_6S$, $C_2H_6S_2$ and $C_8H_8$, are detected by the gas chromatography. It should be noted that the three Chinese national standards of from GB/T14676 to GB/T14678 specify the gas chromatographic detection methods for the last six malodorous pollutants, in which the detectors, the chromatographic columns and the working conditions are different from each other, to one's surprise; actually. It is found that these national standards specify 6 malodorous compounds to be measured by using 2 different sizes of packed columns. This means that a single chromatographic column cannot simultaneously detect the 6 malodorous compounds specified by GB14554. In a word, many factors need to be considered when selecting a suitable chromatographic column, including its material, stationary phase, inner diameter, film thickness, length, as well as the test sample's polarity or non-polarity.

A single-type gas sensor array has poor selectivity, limited overlapping perception range and low sensitivity, and thus does not satisfy the online detection requirement of bio-fermentation, malodorous pollution and other objects. The chromatography has the advantages of high sensitivity and good selectivity, and has the defects of long separation time or detection period, complex instrument structure and harsh working condition, which lead to the existing usages completely not suitable for the online detection of odors. In the absence of spectrograms for either internal or external standard samples, the constituent and components of the unknown samples cannot be determined at all by a single spectrogram measured once. The second defect of the gas chromatography is that the "selectivity" of the chromatographic column is not universal. A specific chromatographic column is sensitive to a specific sample only under a certain condition, i.e. the specific chromatographic column may only detect a specific sample in a specific range. When any one of the following statuses: sampling condition, test condition or chromatographic column parameter changes, the chromatographic perception parameters for a particular sample change accordingly. The third defect of the gas chromatography is that it is difficult and even impossible to achieve a "complete separation" of multi-component chromatographic peaks. The more the components and the closer the polarity and the retention time between the components, the more difficult the complete peak-to-peak separation. It is considered that the "complete separation" situation of multi-component chromatographic peaks in the chromatogram is relative and unusual. Conversely, incomplete separation of multi-component chromatographic peaks is absolute and usual. In terms of operating parameters, they two, to improve chromatographic separation degree and to shorten the retention time, are sometimes contradictory.

The advantages of gas sensors are fast response speed, low working condition requirements, and their disadvantages are poor selectivity and unsatisfactory sensitivity. Compared with that, the advantages of the GC method are high sensitivity and good selectivity, and their defects are long separation time or detection period, complex instrument structure and harsh working condition, and therefore wholly unsuitable to do long-term online detection in their current usage. It should be noted that the difference of "the good selectivity of GC column and the poor selectivity of MOS gas sensors" is only a relative speaking, and the "qualitative ability" of the gas chromatography to unknown samples is still "weak". The gas sensor array and the capillary GC column form distinct contrast, and the fusion of them two can achieve the effect of complement each other. To realize the relatively-wide-range online perception to fermentation processes or malodorous pollutants, the problem to be solved is how to combine the gas sensor array with the chromatographic column to realize their complementary advantages and further realize long-term circulating online detection with a single period of about 5-10 min. In order to realize an online detecting and analyzing method of electronic nose instrument by fusing the gas sensor array with the capillary gas chromatographic column, the following theory and analytical technique problems of odor perception need to be solved.

(A) Multi-Perception Information Selection and Fusion Method of Gas-Sensitivity-and-Chromatography and Online Perception Capability of the Electronic Nose Instrument.

Two characteristics of odors are as follows. (1) Numerous and changing compositions. Take the malodorous pollutants as an example: the most of components are organic substances, or called volatile organic compounds (VOCs), except a few inorganic substances, such as $H_2S$, $NH_3$ and $SO_2$. (2) Some components have a low olfaction threshold, but have a large contribution to the odor intensity, and vice versa. One dilemma encountered by the electronic nose in practical application is that some components contribute little to the odor intensity, but the gas sensor is very sensitive; and vice versa. In order to realize online odor detection, the gas sensors should have such performance indices as high sensitivity, fast response speed, stable working state, high commercial level, long service life, small size and good selectivity. Therefore, the characteristics of different-type gas sensors should be deeply understood, and on this basis, small-type gas sensor array modules are designed, with the purpose to effectively solve such problems as poor stability, noise elimination, temperature and humidity compensation, easy replacement, etc.

A large number of experiments have shown that the MOS gas sensors represented by $SnO_2$ material have a fast response speed to some odors. Only 2 s response duration is spent, for example, to measure an ethanol volatile; however, the response speed will become very slow while testing some other odors, says 60 s or longer. A slow-response example is to sense the volatile of peach aldehyde ($C_{11}H_{20}O_2$), a kind of standard malodorous liquid specified by GB/T14675. This phenomenon tells us that the steady-state maximum values of response curves given by several same-type gas sensors to two odors may be the same, but the peak time points and/or areas under the curves may be different; or conversely, the areas under the curves may be the same, but the steady-state maximum values and the peak time points may be different, etc. In a word, the response curve shapes of a gas sensor are related to odor compositions and many other factors, such as molecular weight, carbon number, polarity, functional group, etc.

The triangular stability refers to such a fact that at least three sides (straight lines) connected head to tail can form a stable structure, and has such a feature that will not deform under pressure. Compared with that, a parallelogram structure is easily deformed under pressure and thus unstable. Similarly, polygons with more than 3 sides are unstable. The triangular stability principle enlightens that only two parameters (such three cases: 2 side lengths, 2 included angles, 1 side length plus 1 included angle) cannot determine a triangle structure. Needless to say, it is not even allowed to determine the triangle structure by knowing only one parameter (two such conditions: 1 side length and 1 included angle) among them.

Inspired by the triangular stability principle, multiple pieces of sensitive information should be extracted simultaneously from a single response curve of a certain gas sensor, for example, to select the maximum "steady state" response value, the peak time value and the area under the curve at the same time is equivalent to improve the selectivity of the electronic nose instrument from the angle of data preprocessing. The chromatographic column response speed is at least one order of magnitude lower than that of the gas sensor, and the complete peak/peak separation action leads the chromatography not to satisfy the online odor detection requirement. Inspired by the marathon life prototype, several highest peaks and the corresponding retention time, as well as the areas under the chromatogram curve may be extracted from the semi-separation chromatogram in a specified interval (say $T_0=10$ min or so), which may be used as the sensitive information features of the capillary chromatogram column for the fermentation objects or malodorous pollutants, so as to improve the response speed or online capability of the gas chromatography.

How to select and fuse multiple pieces of feature information from the response curves of gas sensor array and the semi-separation chromatogram simultaneously to improve online qualitative and quantitative analysis capability of the electronic nose instrument is a main problem to be solved by this disclosure.

(B) Optimal Combination of Functional Units Including the Gas Sensor Array and Integration and Automation of the Electronic Nose Instrument The odor compositions are numerous, and the environment is variable. It is uneconomical, even unrealistic, to use redundant gas-sensitive elements to form an array to detect all types of odors. It has previously pointed out that either a single chromatographic column or a single-type gas sensor array has a limited sensitive range. Therefore, there is an urgent need to provide an optimization and fusion method of a gas sensor array and a gas chromatographic column, which modularizes and integrates an odor perception system, a gas automatic sampling system, a driving and control circuit, a computer and the others into a test box, and in order to develop a multipoint centralized electronic nose instrument with small size, light weight and simple and convenient operation; the working state of each part in the instrument is precisely controlled, the working conditions within the instrument are optimized, and the internal 'invariability' is realized to cope with the external 'variability'. Ideally, one electronic nose instrument may perform a simultaneous online detection, i.e., a fixed point detection or a movable point detection, on multiple fermentation tanks or multiple malodorous pollution observation points in a specific region in a manner of 24 hours a day in year and month units. The simple and effective machine learning models and algorithms are used to realize the real-time online analysis and prediction of the odor intensity and the concentration prediction of the main components, and the WIFI technique is used to transmit the detection data and analysis results to a monitoring center and various terminals in real-time, so as to realize the remote monitoring of the specific regions based on the Internet.

(C) Online Analytical Capability and Intellectualization of the Electronic Nose Instrument Based on Big Data and Machine Learning.

Human society is currently in the era of big data and artificial intelligence. Such big data as health, finance, transportation, commerce, and genetics are profoundly changing people's live and work ways. In our country, the setup of big ecological environment data has been put on the agenda, and many governmental environmental protection departments are vigorously promoting it.

It is unrealistic to estimate the intensities of complex odors and the concentrations of multiple components online by either a single-type gas sensor array, or a single gas chromatographic column or a single machine learning model without multi-source perception data generated by the online test of massive odors, olfactory discrimination data, and component detection data of conventional instruments such as gas chromatography/mass spectrometry. Although many electronic noses do this, the effect of the resulting detection data is very limited and the final results are therefore unreliable.

Because of odor complexity and environmental variability, a small dataset is not sufficient to effectively train a machine learning model to identify multiple odor types and quantitatively predict complex odor constituents. Big odor data should be established on the basis of conventional instrument detection data such as gas sensitive/gas chromatography multi-source perception data, smelling data and gas chromatography/mass spectrometry. With the big odor data, the machine learning method can identify the odor types and quantitatively predict the concentrations of multiple components through data mining algorithms according to the current perception information. Big data and online complex multi-component prediction of odors are two contradictory aspects, and an effective scheme is to realize type identification of odors and real-time quantitative prediction of their intensities and concentrations of multiple main components through deep research and effective adoption of a machine learning model with algorithm which are as simple and effective as possible.

REFERENCES

[1] P. Boeker, On 'Electronic Nose' methodology, *Sensors &Actuators B—Chemical*, 2014, 204: 2-17.

SUMMARY

The present disclosure is based on existing invention patents of "an online multi-point centralized monitoring and analyzing system and method for malodorous gases" (see Chinese patent application No: 2018104716131), "a method for online multi-point centralized analyzing big data driven malodorous gases by using electronic nose instrument" (see Chinese patent application No. 2018104717083) and "a multi-channel integrated olfactory analog instrument and a method for online analyzing bio-fermentation process" (see Chinese patent application No: 201310405315X), and provides an electronic nose instrument and a method for online detecting and analyzing multiple state parameters in fermentation and malodorous pollution processes by using a combinative electronic nose instrument of gas sensitivity and gas chromatography, to solve the problems of long-term online detection, type identification and online quantitative prediction of an qualitative intensity index and various compound concentration control index values of multiple fermentation processes or multiple malodorous pollution points.

To achieve the above objectives, the present disclosure provides the following technical schemes.

The electronic nose instrument includes a gas sensor array module I, a capillary gas chromatographic column module II, a gas auto-sampling module III, a computer control and analysis module IV and an auxiliary gas source V, which is configured to perform cyclically long-term online detection and intelligent analysis of multiple bio-fermentation processes or multiple malodorous pollution processes.

The gas sensor array module I includes a gas sensor array I-1, an annular working chamber I-2 for installing the gas sensor array I-1, a resistance heating element I-3, a fan I-4, a thermal insulation layer I-5 and a partition plate I-6 and is located in a middle right side of the electronic nose instrument.

The capillary gas chromatographic column module II includes a capillary gas chromatographic column II-1, a detector II-2, an amplifier II-3, a recorder II-4, a sampling inlet II-5, a resistive heating wire II-6, a fan II-7 and a thermal insulation layer II-8 and is located in an upper right side of the electronic nose instrument.

The gas auto-sampling module III includes a first two-position two-port electromagnetic valve III-1, a second two-position two-port electromagnetic valve III-2, a third two-position two-port electromagnetic valve III-3, a fourth two-position two-port electromagnetic valve III-4, a fifth two-position two-port electromagnetic valve III-5, 5 first purifiers III-6, a first miniature vacuum pump III-7, a first flowmeter III-8, a sixth two-position two-port electromagnetic valve III-9, a first throttle valve III-10, a two-position three-port electromagnetic valve III-11, a three-position four-port electromagnetic valve III-12, a second miniature vacuum pump III-13, a seventh two-position two-port electromagnetic valve III-14, an eighth two-position two-port electromagnetic valve III-15, a pressure stabilizing valve III-16, a first pressure reducing valve III-17, a second throttle valve III-18, a second purifier III-19, a second pressure reducing valve III-20, a third purifier III-21, a third throttle valve III-22, a second flowmeter III-23, a fourth throttle valve III-24 and a fifth throttle valve III-25 and is located in a lower right side of the electronic nose instrument.

The computer control and analysis module IV includes a computer mainboard IV-1, an A/D data acquisition card IV-2, a driving and control circuit board IV-3, a 4-path precision direct-current stabilized voltage power supply IV-4, a display IV-5 and a WIFI module IV-6 and is located in a left side of the electronic nose instrument.

One bio-fermentation process/fermentation tank or one malodorous pollution point is referred to as one monitoring point; the single gas sampling period of the electronic nose instrument at one monitoring point is $T_0$=300-600 s, and is $T_0$=480 s by default. In the single gas sampling period $T_0$, a tested gas at one monitoring point is respectively sucked into the gas sensor array module I and the capillary gas chromatographic column module II by the first miniature vacuum pump III-7 and the second miniature vacuum pump III-13; the gas sensor array I-1 and the capillary gas chromatographic column II-1 generate a sensitive response; and thus, the electronic nose instrument obtains a group of response curves of the gas sensor array and a gas chromatogram, which is a gas sensitivity/gas chromatography simulation signal obtained by perceiving a tested gas sample using the electronic nose instrument.

In the single gas sampling period $T_0$, the computer control and analysis module IV selects 3 perception information from each voltage response curve with a duration of 60 s of the gas sensor array I-1 to satisfy a triangular stability principle and improve the qualitative and quantitative capacity of the gas sensor array, where the 3 perception information includes a steady-state peak value $v_{gsi}(\tau)$, peak time $t_{gsi}(\tau)$ corresponding to the $v_{gsi}(\tau)$, and an area $A_{gsi}(\tau)$ under the voltage response curve. In a case where the gas sensor array I-1 includes 16 gas sensors, i=1,2, . . . , 16, the computer control and analysis module IV obtains 16*3=48 perception component in total from 16 response curves of the gas sensor array in the single gas sampling period $T_0$.

In the single gas sampling period $T_0$, in a case where the electronic nose instrument does not pursue a complete between-peak separation of a gas chromatogram, the computer control and analysis module IV selects 21 perception component from a semi-separation gas chromatogram to improve the online detection capability of the gas chromatographic column, where the 21 perception components include first 10 maximum chromatographic peak values $v_{gcj}(\tau)$, 10 retention time $h_{gcj}(\tau)$ corresponding to the first 10 maximum chromatographic peak values, and an area $A_{gc}(\tau)$ under a whole chromatogram curve.

In the single gas sampling period $T_0$, the electronic nose instrument perceives tested gas in one bio-fermentation process or at one malodor pollution point; and the computer control and analysis module IV fuses 48 perception components extracted from the 16 response curves of the gas sensor array I-1 and 21 perception components extracted from the semi-separation chromatogram of the capillary gas chromatographic column II-1 to obtain a perception vector $x(\tau) \in R^{69}$ with m=48+21=69 dimensions, where the perception vector $x(\tau) \in R^{69}$ is referred to as a sample; and it is used as a basis of doing a qualitative and quantitative analysis on a bio-fermentation process or a malodorous pollution process by the electronic nose instrument.

The electronic nose instrument sets a cyclical gas sampling period for n(≤5) bio-fermentation processes or n(≤5) malodorous monitoring points to be $T=nT_0$; the electronic nose instrument obtains n samples in sequence, the n samples are saved in n data files of a computer hard disk corresponding to the n samples respectively, and then sample data is sent to a cloud terminal and a specifically fixed/mobile terminal through the WIFI routing module. If $T_0=480$ s, then the cyclical tested gas sampling period is $T=nT_0=n*480$ s, which is equivalent to detect once in every other n*480 s for one fermentation tank or one malodorous pollution point being detected every n*480 s.

The electronic nose instrument forms the main body of big odor data X through a long-term online detection of the multiple bio-fermentation processes and multiple malodorous pollution points over years; where the data set X further includes offline detection data of a gas chromatography instrument, a mass spectrometry instrument and a spectrophotometric instrument, odor unit (OU) concentration data obtained through laboratory sensory smelling, and bio-fermentation type data of penicillin, erythromycin, vinegar, soy sauce, cooking wine and monosodium glutamate recorded by on-site operators, and malodorous pollution monitoring region type data of a chemical industrial park, a refuse landfill, a sewage treatment plant and a livestock and poultry farm; a part of subsets of the data set X establish a corresponding relationship between a response vector of gas sensor array and gas chromatography and the multiple types of bio-fermentation processes/malodorous pollution points including a main component concentration.

In the learning stage, each perception component of the big odor data X is made to be normalized, a machine learning model of the computer control and analysis module IV offline learns the big odor data X to determine the structure and parameters of the machine learning model. In the decision-making stage, the machine learning model online leans recent responses of gas sensitive and gas chromatography to finely tune the parameters of the machine learning model, online determines the types of the multiple bio-fermentation processes and malodorous pollutions, and quantitatively predicts the concentrations of main chemical compositions of fermentation liquids during the bio-fermentation processes or 8+1 concentration index values of malodorous pollutants, including 8 specified chemical components, ammonia ($NH_3$), hydrogen sulfide ($H_2S$), carbon disulfide ($CS_2$), trimethylamine ($C_3H_9N$), methyl mercaptan ($CH_4S$), methyl sulfide ($C_2H_6S$), dimethyl disulfide ($C_2H_6S_2$) and styrene ($C_8H_8$) specified by the Chinese national standard GB14554, as well as an OU concentration value, by depending upon a group of time-serial response patterns of gas sensor array and gas chromatography.

The gas sensor array I-1 and the annular working chamber I-2 are located in a thermostatic box with a temperature of 55±0.1° C. In the single gas sampling period $T_0$, the gas sensor array module I is made to be sequentially subject to 6 stages, i.e., a rough recovery stage of the gas sensor array for $T_0$–120 s, an accurate calibration stage by dry air for 40 s, a balance stage for 5 s, a headspace sampling stage of tested gas for 60 s, a transition stage for 5 s and a flushing stage by clean ambient air for 10 s. Gas types and flow rates for these 6 stages are in order: (i) clean ambient air of 6,500 ml/min; (ii) dry air of 1,000 ml/min; (iii) no gas flow; (iv) tested gas of 1,000 ml/min; (v) clean ambient air of 1,000 ml/min; (vi) clean ambient air of 6,500 ml/min; where "transition" mainly refers to a change from the tested gas to the clean ambient air.

An interval of [$T_0$–75 s, $T_0$–15 s] in the single gas sampling period $T_0$ is the headspace sampling stage of the gas sensor array module I for the tested gas, one two-position two-port electromagnetic valve III-k (k=1,2, . . . , 5) among the first two-position two-port electromagnetic valve III-1 is set to the fifth two-position two-port electromagnetic valve III-5 to be on, the three-position four-port electromagnetic valve III-12 is set to be "0", the sixth two-position two-port electromagnetic valve III-9 is set to be off, the seventh two-position two-port electromagnetic valve III-14 is set to be off, and the eighth two-position two-port electromagnetic valve III-15 is set to be on; and under the suction action of the first miniature vacuum pump III-7, a tested gas at one monitoring point is made to sequentially flow through, at a flow rate of 1,000 ml/min, the $k^{th}$ two-position two-port electromagnetic valve III-k (k=1, 2, . . . , 5), the eighth two-position two-port electromagnetic valve III-15, the pressure stabilizing valve III-16, the annular working chamber I-2, the gas sensor array I-1, the first throttle valve III-10 and the first flowmeter III-8, and finally, the tested gas is discharged to outdoor by lasting 60 s, and therefore, the gas sensor array I-1 generates a sensitive response to the tested gas, and the sensitive response is stored in a temporary file of the computer control and analysis module IV.

An interval of [$T_0$–120 s, $T_0$–80 s] of the single gas sampling period $T_0$ is the accurate calibration stage of the gas sensor array module I by the dry air, the three-position four-port electromagnetic valve III-12 is set to be "1", the sixth two-position two-port electromagnetic valve III-9, the seventh two-position two-port electromagnetic valve III-14, and the eighth two-position two-port electromagnetic valve III-15 are set to be off; and dry air in the dry air bottle V-2 is made to sequentially flow through, at a flow rate of 1,000 ml/min, the first pressure reducing valve III-17, the second throttle valve III-18, the second purifier III-19, the three-position four-port electromagnetic valve III-12, the pressure stabilizing valve III-16, the annular working chamber I-2, the gas sensor array I-1, the first throttle valve III-10 and the first flowmeter III-8, and finally, the dry air is discharged to outdoor by lasting 40 s. During this period, the gas sensor array I-1 is made to accurately restore to a reference state under the role of the dry air. As the eighth two-position two-port electromagnetic valve III-15 is set to be off, whether the first two-position two-port electromagnetic valve III-1 to the fifth two-position two-port electromagnetic valve III-1 are off or on does not affect a calibration of the gas sensor array I-1.

The "clean ambient air" is the kind of the outdoor air in where the electronic nose instrument is located by the dust removal, dehumidification and aseptic pretreatments, the clean ambient air is only used for the rough recovery of the gas sensor array I-1, flushing inner walls of the annular working chamber I-2 as well as related pipelines, and taking away the accumulated heat volume generated by the gas sensor array I-1. In two intervals of [0, $T_0$–120 s] and [$T_0$–10 s, $T_0$] of the single gas sampling period $T_0$, the three-position four-port electromagnetic valve III-12 is set to be "2", the sixth two-position two-port electromagnetic valve III-9 is set to be on, and the eighth two-position two-port electromagnetic valve III-15 is set to be off; and the clean ambient air is made to sequentially flow through, at a flow rate of 6,500 ml/min, the three-position four-port electromagnetic valve III-12, the pressure stabilizing valve III-16, the annular working chamber I-2, the gas sensor array I-1, the sixth two-position two-port electromagnetic valve III-9 and the first flowmeter III-8, and finally, the clean ambient air is discharged to outdoor by lasting $T_0$–110 s. During this period, the gas sensor array I-1 is made to roughly recover to a reference state under the role of the clean ambient air; as the eighth two-position two-port electromagnetic valve III-15 is set to be off, whether the first two-position two-port electromagnetic valve III-1 to the fifth two-position two-port electromagnetic valve III-1 are off or on does not affect a rough recovery of the gas sensor array I-1.

A size of a commercially available capillary gas chromatographic column II-1 is set to be a length 'L' times an inner diameter 'φd' times a film thickness 'δ', namely L×φd×=30 m×φ0.53 mm×0.25 μm, by default, and is located in a thermostatic box with a temperature of 250-300±0.1° C. In the single gas sampling period $T_0$, the capillary gas chromatographic column module II sequentially undergo three stages, i.e., a headspace sampling stage of the tested gas for Is, a chromatographic separation stage of the tested gas for $T_0$–16 s, and an emptying and purging stage for 15 s; where $H_2$ is also used as a carrier gas and a fuel gas, and a dry air is used as a combustion-supporting gas.

The initial is of the single gas sampling period $T_0$ is the headspace sampling stage of the tested gas by the capillary gas chromatographic column module II, one two-position two-port electromagnetic valve III-k (k=1,2, . . . , 5) among the first two-position two-port electromagnetic valve III-1 to the fifth two-position two-port electromagnetic valve III-5 is set to be on, the two-position three-port electromagnetic valve III-11 is set to be "1", the seventh two-position two-port electromagnetic valve III-14 is set to be on, and the eighth two-position two-port electromagnetic valve III-15 is set to be off. At the moment, under the suction action of the second miniature vacuum pump III-13, tested gas at a monitoring point k is made to sequentially flow through the one two-position two-port electromagnetic valve III-k (k=1, 2, . . . , 5) among the first two-position two-port electromagnetic valve III-1 to the fifth two-position two-port electromagnetic valve III-5, the seventh two-position two-port electromagnetic valve III-14, the two-position three-port electromagnetic valve III-11 and the fourth throttle valve III-24, and it is mixed with the carrier gas $H_2$ at the sampling inlet II-5 to flow into the capillary gas chromatographic column II-1 and last for 1 s, where a sampling flow rate of the tested gas is 6 ml/min by default, a sampling duration is 1 s by default, and an cumulative sampling amount is 0.1 ml by default.

An interval of [1 s, $T_0$–10 s] in the single gas sampling period $T_0$ is the chromatographic separation stage of the capillary gas chromatographic column module II for the tested gas, and the two-position three-port electromagnetic valve III-11 is set to be "2", and the seventh two-position two-port electromagnetic valve III-14 is set to be off, so that tested gas from the monitoring point k cannot enter the gas chromatographic column module II for $T_0$–11 s. Under the pushing action of the carrier gas $H_2$ with a certain pressure and a certain flow rate, the tested gas is injected into the sampling inlet II-5 of the gas chromatographic column module II are separated in the capillary gas chromatographic column II-1, a perception response is generated through the detector II-2, the perception response is amplified through the amplifier II-3, the recorder II-4 records the perception response within an interval of [0, $T_0$–10 s], i.e., a duration of $T_0$–10 s of the chromatographic column II-1, and the perception response is saved within the interval of [0, $T_0$–10 s] in a temporary file of the computer control and analysis module IV.

An interval of [$T_0$–10 s, $T_0$] with a duration of 10 s in the single gas sampling period $T_0$ is an emptying and purging stage of the capillary gas chromatographic column II-1, the one two-position two-port electromagnetic valve III-k in an originally on state among the first two-position two-port electromagnetic valve III-1 to the fifth two-position two-port electromagnetic valve III-5 is set to be off, and one of four two-position two-port electromagnetic valves in an originally off state among the first two-position two-port electromagnetic valve III-1 to the fifth two-position two-port electromagnetic valve III-5 is set to be on; the two-position three-port electromagnetic valve III-11 is set to be "2", the seventh two-position two-port electromagnetic valve III-14 is set to be on, the eighth two-position two-port electromagnetic valve III-15 is set to be off. Assuming that the two-position two-port electromagnetic valve III-(~k) is on (k=1, 2, . . . , 5), under the suction action of the second micro vacuum pump III-13, a tested gas is made to sequentially flow through, at a flow rate of 330 ml/min, the two-position two-port electromagnetic valve III-(~k), the seventh two-position two-port electromagnetic valve III-14 and the two-position three-port electromagnetic valve III-11, and finally, the tested gas is discharged to outdoor directly, so that gas residues from a monitoring point k in a current gas sampling period of a related pipeline is removed, and the pipeline is gradually filled with the tested gases from the monitoring point ~k to prepare a detection of next bio-fermentation process or malodorous pollution monitoring point in a next gas sampling period, and a detection duration is 10 s.

An interval of [$T_0$–10 s, $T_0$] of the single gas sampling period $T_0$ is still an information selection and analysis time stage, the computer control and analysis module IV selects 48 pieces of perception information including a group of steady-state peak values $v_{gsi}(\tau)$, i=1,2, . . . 16 from a group of voltage response curves of the gas sensor array I-1 obtained in an interval of [$T_0$–75 s, $T_0$–15 s]. 21 perception components including the first 10 maximum chromatographic peak values $v_{gcj}(\tau)$, j=1,2, . . . 10 are selected from a chromatogram obtained in an interval of [0, $T_0$–10 s]. It is used as a basis of further doing an analysis on a bio-fermentation process or a malodorous pollution region by the electronic nose instrument. The computer control and analysis module IV performs a type identification of an odor and a quantitative prediction its overall intensity as well as the main concentration index values according to the current pattern vector x(τ) and the big odor data X.

In the single gas sampling period $T_0$, in a case where one bio-fermentation process or one malodorous pollution point is detected only, the cyclical tested gas sampling period is made to be $T=T_0$. In a case where k bio-fermentation processes or malodorous pollution points are simultaneously detected in sequence in the specified time stage, the cyclical sampling period for one of multiple tested gas samples from the k bio-fermentation processes and/or malodorous pollution points is made to be $T=k*T_0$. In a case where the one of the k bio-fermentation processes and/or malodorous pollution points exits from the current long-term circulation monitoring process, the cyclical sampling period change of tested gas samples is made to be changed into $T=(k-1)*T_0$ from the original $T=k*T_0$. Similarly, in the long-term circulation monitoring process, in a case where a new bio-fermentation processes or malodorous pollution point is added to the present long-term circulation detection process in the midway, the cyclical sampling period of tested gas samples is made to change into $T=(k+1)*T_0$, where a corresponding data recording period is changed from the moment while one bio-fermentation process or one malodorous pollution point exits or joins.

In the single gas sampling period $T_0$, an interval of $[T_0-10$ s, $T_0]$ is an information selection and analysis stage with a duration of 10 s, the computer control and analysis module IV performs information selection and analysis operations on the gas sensor array module I and the capillary gas chromatographic column module II. The computer control and analysis module IV selects 3 components of perception information, i.e., a steady-state peak value $v_{gsi}(\tau)$, a corresponding peak time $t_{gsi}(\tau)$ and an area under the curve $A_{gsi}(\tau)$ from the $i^{th}$ voltage response curve of the gas sensor array I-1 obtained in an interval of $[T_0-75$ s, $T_0-15$ s$]$ with a duration of 60 s; the computer control and analysis module IV selects 21 perception response components, i.e., the first 10 maximum chromatographic peak values $v_{gcj}(\tau)$, the 10 retention time $t_{gcj}(\tau)$ corresponding to the first 10 maximum chromatographic peak values, and the 1 area $A_{gc}(\tau)$ under the semi-separation chromatogram curve from the capillary gas chromatographic column II-1 in an interval of $[0, T_0-10$ s$]$, i.e., a duration of 6 s; and the 21 perception response components are saved in a temporary file of the computer hard disk.

In the single gas sampling period $T_0$, in a case where the number q of chromatographic peaks of the semi-separation chromatogram with a duration of $T_0-10$ s is less than 10, or q<10, the computer control and analysis module IV selects the first q<10 maximum chromatographic peak values $h_{gcj}(\tau)$, the corresponding q<10 retention time values $t_{gcj}(\tau)$, and 1 area under the chromatogram curve $A_{gc}(\tau)$, all from the semi-separation chromatogram, and then a zero-filling operation is performed to the insufficient peak values and the corresponding retention time values; where the obtained chromatogram perception information is $x_{gc}(\tau)=\{(h_{gc1}(\tau), h_{gc2}(\tau), \ldots, h_{gcq}(\tau), 0, \ldots, 0); (t_{gc1}(\tau), t_{gc2}(\tau), \ldots, t_{gcq}(\tau), 0, \ldots, 0); A_{gc}(\tau)\}$.

A last 10 s of the single gas sampling period $T_0$ is an information processing and analysis interval of $[T_0-10$ s, $T_0]$, a modular machine learning model of the computer control and analysis module IV performs a type identification of an odor and a quantitative prediction of its overall intensity as well as many concentration index values of main components on a bio-fermentation process and/or malodorous pollution point based on a recent time-series response matrix X(τ−q) given by a gas sensitivity and a gas chromatography, the method includes: a type of bio-fermentation process and a malodorous pollution point are identified; a quantitative concentration estimation is performed on cells, substrates and even bio-products in the multiple bio-fermentation processes; for instance, a quantitative concentration estimation is performed on such precursor substances as n-propanol and phenylacetic acid in different fermentation processes; and a quantitative concentration prediction is performed on (8+1) kinds of malodorous pollutants specified by GB14554, where τ is a current time point, q is a recently elapsed time point, and r-q is a recent interval.

Also included in the big odor data X are: the gas sensitive/gas chromatographic data sensitized by an electronic nose instrument for multiple headspace vapors of simple compounds with a concentration of 0.1 ppm to 10000 ppm; offline detection data of a gas chromatographic, a mass spectrometric and a spectrophotometric instrument; professional laboratory olfactory data; and especially multiple simple compounds not only include such precursor substances as n-propanol, phenylacetic acid in the bio-fermentation processes; but also includes 8 malodorous compounds specified by GB14554; and the standard reference substance of odor concentration (OU) value, butanol, specified by the European standard EN13725.

The machine learning model includes multiple modular deep convolutional neural networks; the number of the modular single-output deep convolutional neural networks are equal to either the main predicted component number of fermentation liquors in the multiple bio-fermentation processes plus the objective odor-type number detected, or the main concentration index number of malodorous pollutants plus the objective odor-type number, each for one. One single-output deep convolutional neural network in the multiple modular single-output deep convolutional neural networks includes 1 input layer, 3 convolutional layers, 2 down-sampling layers and 1 output unit, and activation functions in each convolutional layer, each down-sampling layer and the output layer are all a Sigmoid correction activation function $f(\varphi)=3(1+\exp(-\varphi/3))^{-1}$. In the learning stage, the each single-output deep convolutional neural network adopts an offline layer-wise error back-propagation algorithm to mainly learn the big odor data X with labels and/or known components; a scan window in each convolutional layer is set to be 55, and an overlapping scan step length is set to be 1; 6 single-type kernels, a sine, a cosine, a polynomial, a Gaussian, a Sigmoid, a wavelet and a Laplace kernel are made to form a group of combined convolution kernels; a scan window in each down-sampling layer is set to be 2×2, a non-overlapping scan step length is set to be 2, and such 3 features as a maximum, a mean and a mean-square-error value are extracted; and in the decision-making stage, n single-output deep convolutional neural network models perform an odor type identification, and an intensity estimation and prediction of their intensities and main component concentrations one by one at a current time point r and coming τ+1, τ+2 and τ+3, according to a current gas sensitive/gas chromatographic response vector x(τ) and a recently occurred time-series response matrix X(τ−q).

By means of the gas-sensitive-gas-chromatographic electronic nose instrument and the online analysis method of multiple state parameters of fermentation and malodorous pollutant processes of the present disclosure, that the electronic nose instrument performs a long-term online circulation detection and an online analysis prediction of multiple bio-fermentation processes/malodorous pollution points includes the following steps:

(1) Power-on operation: performing a preheating operation in the electronic nose instrument for 30 min.

The single gas sampling period $T_0$ in a screen menu is set as a default value $T_0$=8 min, and a cyclical gas sampling period for 5 monitoring points is set to be $T=5T_0$.

The three-position four-port electromagnetic valve III-12 is set to be "2", the sixth two-position two-port electromagnetic valve III-9 is set to be on and the eighth two-position two-port electromagnetic valve III-15 is set to be off, under the suction action of the first miniature vacuum pump III-7, clean ambient air is made to sequentially flow through, at a flow rate of 6,500 ml/min, the three-position four-port electromagnetic valve III-12, the pressure stabilizing valve III-16, the annular working chamber I-2, the gas sensor array I-1, the sixth two-position two-port electromagnetic valve III-9 and the first flowmeter III-8, and finally, the clean ambient air is discharged to outdoor. Therefore, the annular working chamber for installing the gas sensor array I-1 reaches a constant internal temperature of 55+0.1° C.

The two-position three-port electromagnetic valve III-11 is set to be "2", and the seventh two-position two-port electromagnetic valve III-14 is set to be off. Under the pushing role of the carrier gas $H_2$, the capillary gas chromatographic column II-1 is made to gradually recover to a reference state, and thus the chromatographic column box reaches a constant internal temperature of 250±0.1° C.

(2) Beginning a cyclical gas sampling period:

An option with "monitoring point k on" in a screen menu of the display IV-5 is clicked, where k=1, 2, . . . , 5, the electronic nose instrument performs a continuous and cyclical detection until the operator clicks an option with "monitoring point k off"; in a process that the electronic nose instrument performs a cyclical detection on the 5 monitoring points in order, the computer control and analysis module IV automatically generates 5 text files respectively to save the sensitive response data of the gas sensor array I-1 and the capillary gas chromatographic column module II to the tested gases at the 5 monitoring points.

(3) Beginning the single gas sampling period at a monitoring point k among the 5 monitoring points: a default period value $T_0$=8 min is taken as an example:

(3.1) For the gas sensor array module I: the following six gas sampling stages are undergone in order, i.e., (i) a rough recovery stage for 360 s, (ii) an accurate calibration stage for 40 s, (iii) a balance stage for 5 s, (iv) a headspace sampling stage for 60 s, (v) a transition stage for 5 s, and (vi) a cleaning and rough recovery stage for 10 s.

(3.1a) The rough recovery stage from 0 s to the $360^{th}$ sec of the single gas sampling period $T_0$.

The three-position four-port electromagnetic valve III-12 is set to be "2", the sixth two-position two-port electromagnetic valve III-9 is set to be on, and the eighth two-position two-port electromagnetic valve III-15 is set to be off. Under the suction action of the first miniature vacuum pump III-7, the clean ambient air is made to flow through, at a flow rate of 6,500 ml/min, the three-position four-port electromagnetic valve III-12, the pressure stabilizing valve III-16, the annular working chamber I-2, the gas sensor array I-1, the sixth two-position two-port electromagnetic valve III-9 and the first flowmeter III-8 in order, and finally, the clean ambient air is discharged to outdoor. Therefore, the gas sensor array I-1 is made to initially recover to a reference state.

(3.1b) For the accurate calibration stage from the $360^{th}$ sec to the $400^{th}$ sec of the single gas sampling period $T_0$.

The three-position four-port electromagnetic valve III-12 is set to be "1", the sixth two-position two-port electromagnetic valve III-9 is set to be off, the seventh two-position two-port electromagnetic valve III-14 is set to be off, and the eighth two-position two-port electromagnetic valve III-15 is set to be off. Under the suction action of the first miniature vacuum pump III-7, dry air is made to flow through, at a flow rate of 1,000 ml/min, the first pressure reducing valve III-17, the second throttle valve III-18, the second purifier III-19, the three-position four-port electromagnetic valve III-12, the pressure stabilizing valve III-16, the annular working chamber I-2, the gas sensor array I-1 in the annular working chamber I-2, the first throttle valve III-10 and the first flowmeter III-8 in order, and finally, the dry air is discharged to outdoor by lasting 40 s. Therefore, the gas sensor array I-1 is made to accurately recover to a reference state.

(3.1c) For the balance stage from the $400^{th}$ sec to the $405^{th}$ sec of the single gas sampling period $T_0$.

The three-position four-port electromagnetic valve III-12 is set to be "0", the sixth two-position two-port electromagnetic valve III-9 is set to be off, and the eighth two-position two-port electromagnetic valve III-15 is set to be off, so that no gas flows in the annular working chamber I-2 for 5 s.

(3.1d) For the headspace sampling stage from the $405^{th}$ sec to the $465^{th}$ sec of the single gas sampling period $T_0$.

The two-position two-port electromagnetic valve III-k (k=1,2, . . . , 5) among the first two-position two-port electromagnetic valve III-1 to the fifth two-position two-port electromagnetic valve III-5 is set to be on, the three-position four-port electromagnetic valve III-12 is set to be "0", the sixth two-position two-port electromagnetic valve III-9 is set to be off, the seventh two-position two-port electromagnetic valve III-14 is set to be off, and the eighth two-position two-port electromagnetic valve III-15 is set to be on. Under the suction action of the first miniature vacuum pump III-7, the tested gas at a monitoring point is made to flow through, at a flow rate of 1,000 ml/min, the two-position two-port electromagnetic valve III-k (k=1,2, . . . , 5), the eighth two-position two-port electromagnetic valve III-15, the pressure stabilizing valve III-16, the annular working chamber I-2 and the gas sensor array I-1, the first throttle valve III-10 and the first flowmeter III-8 in order, and finally, the tested gas is discharged to outdoor by lasting 60 s. Therefore, the gas sensor array I-1 generates a sensitive response, and the sensitive response is saved in a temporary file corresponding to the computer control and analysis module IV.

(3.1e) For the transition stage from the $465^{th}$ sec to the $470^{th}$ sec of the single gas sampling period $T_0$.

The three-position four-port electromagnetic valve III-12 is set to be "2", the eighth two-position two-port electromagnetic valve III-15 is set to be off, the sixth two-position two-port electromagnetic valve III-9 is set to be off, and the seventh two-position two-port electromagnetic valve III-14 is set to be off. Under the suction action of the first miniature vacuum pump III-7, the clean ambient air is made to flow through, at a flow rate of 1,000 ml/min, the three-position four-port electromagnetic valve III-12, the pressure stabilizing valve III-16, the annular working chamber i-2 and the gas sensor array I-1, the sixth two-position two-port electromagnetic valve III-9 and the first flowmeter III-8 in order, and finally, the ambient air is discharged to outdoor;

(3.1f) For the cleaning and rough recovery stage from the $470^{th}$ sec to the $480^{th}$ sec of the single gas sampling period $T_0$.

Compared with the "transition stage", the positions of the rest valves are the same except that the sixth two-position two-way electromagnetic valve III-9 is changed from "off" to "on". The flow rate of the clean ambient air thus is changed from "1,000 ml/min" to "6,500 ml/min"; and a valve position and a working state of the stage is made to be completely the same and match with a valve position and a working state of a "rough recovery" stage of a next gas sampling period.

(3.2) For a capillary gas chromatographic column II module, (i) a headspace sampling stage for 1 s, (ii) a chromatographic separation stage for 469 s and (iii) an emptying and cleaning stage for 10 s are sequentially undergone.

(3.2a) For the headspace sampling stage from 0 s to the $1^{st}$ sec of the single gas sampling period $T_0$.

One of the five two-position two-port electromagnetic valve III-k (k=1,2, . . . , 5) among the first two-position two-port electromagnetic valve III-1 to the fifth two-position two-port electromagnetic valve III-5 is set to be on, the two-position three-port electromagnetic valve III-11 is set to be "1", the seventh two-position two-port electromagnetic valve III-14 is set to be on, and the eighth two-position two-port electromagnetic valve III-15 is set to be off. Under the suction action of the second miniature vacuum pump III-13, the tested gas at a monitoring point k is made to flow through the $k^{th}$ two-position two-port electromagnetic valve III-k (k=1,2, . . . , 5), the seventh two-position two-port electromagnetic valve III-14, the two-position three-port electromagnetic valve III-11 and the fourth throttle valve III-24 in order, and the carrier gas $H_2$ is mixed at the sampling inlet II-5 to flow into the capillary gas chromatographic column II-1 for 1 s.

(3.2b) For the chromatographic separation stage from the $1^{st}$ sec to the $470^{th}$ sec of the single gas sampling period $T_0$.

The two-position three-port electromagnetic valve III-11 is set to be "2", and the seventh two-position two-port electromagnetic valve III-14 is set to be off. Under the pushing role of carrier gas $H_2$ with a certain pressure and flow, the tested gas is separated in the capillary gas chromatographic column II-1, a perception response is generated through the detector II-2, the perception response is amplified through the amplifier II-3, the recorder II-4 records the perception response at a duration of 470 s within an interval of [0, 470 s] to form a semi-separation chromatographic peak graph. The semi-separation chromatographic peak graph is saved in a temporary file corresponding to the computer control and analysis module IV.

(3.3) Information selection and analysis operation, in a time stage from the $470^{th}$ sec to the $480^{th}$ sec of the single gas sampling period $T_0$.

The computer control and analysis module IV selects 3 pieces of sensitive information, i.e., a steady-state peak value $v_{gsi}(\tau)$, a corresponding peak time $t_{gsi}(\tau)$, and an area under the whole curve $A_{gsi}(\tau)$ from a single voltage response curve which is obtained by each gas sensor in an interval of [405 s, 465 s] and lasts for 60 s, to obtain 16*3=48 pieces of sensitive information by the gas sensor array I-1 including 16 gas sensors. The computer control and analysis module IV simultaneously selects first 10 maximum chromatographic peak values $v_{gcj}(\tau)$, 10 corresponding retention time values $t_{gcj}(\tau)$, and an area under a total chromatogram curve $A_{gc}(\tau)$ from the semi-separation chromatogram with a duration of 470 s by the capillary gas chromatographic column module II, to obtain 21 pieces of perception information; the computer control and analysis module IV obtains 1 response vector $x(\tau) \in R^{69}$ with 69 dimensions from the sensitive information of the gas sensor array module I and the capillary chromatography column module II in the signal gas sampling period $T_0$. A machine learning model performs an odor type identification and an overall intensity and main component quantitative prediction based on the sensitive vector $x(\tau)$ and the big odor data X, the monitor displays the detection and prediction results, and then transmit them to a central control room and multiple fixed/mobile terminals through the Internet network.

(3.4) Ending the Current Monitoring Point k and Beginning a Next Monitoring Point.

The $k^{th}$ two-position two-port electromagnetic valve III-k (k=1,2, . . . , 5) among the first two-position two-port electromagnetic valve III-1 to the fifth two-position two-port electromagnetic valve III-5 is set to be from 'on' to 'off', and the two-position two-port electromagnetic valve corresponding to a next monitoring point among the first two-position two-port electromagnetic valve III-1 to the fifth two-position two-port electromagnetic valve III-5 is set to be on.

(4) Repeat the steps (3.1)~(3.4), and the electronic nose instrument realizes online cyclical detection, identification and quantitative prediction of odor intensity and multiple concentration index values of the tested gases at the 1~5 monitoring points.

DETAILED DESCRIPTION

The present disclosure will be further described in details below with the above accompanying drawings.

Figure 1:
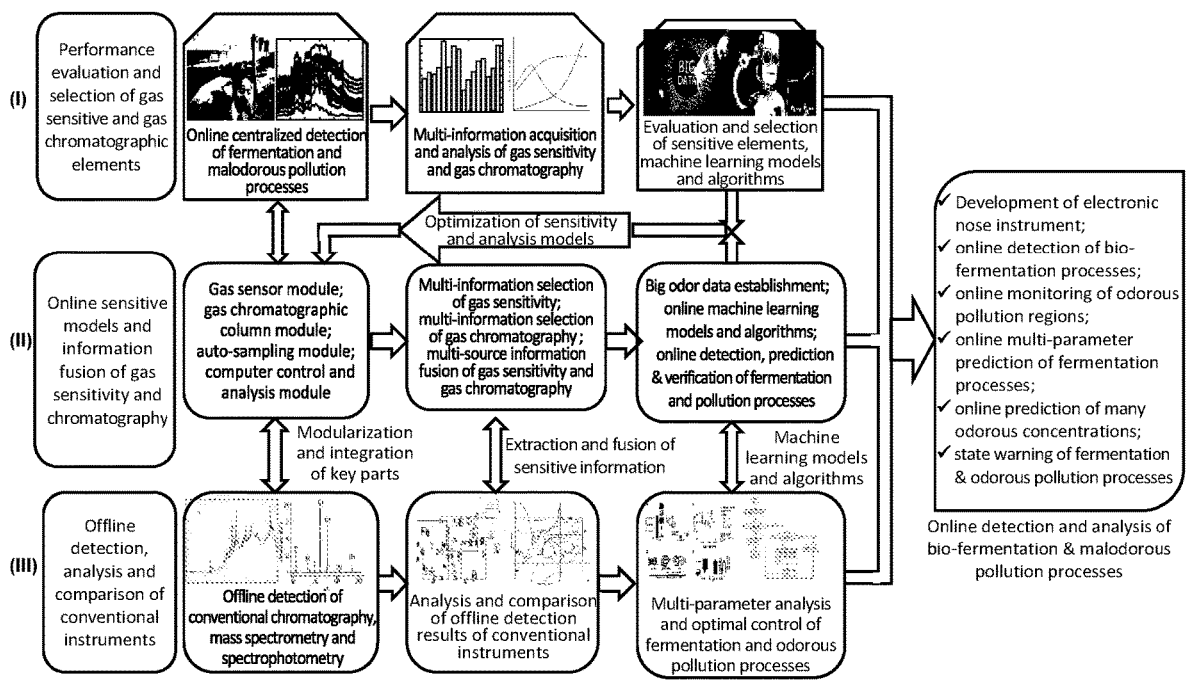
FIG. 1 is a schematic diagram of a technical route of gas sensitive/gas chromatographic multi-perception information fusion, electronic nose instrument development, fermentation tail gas and malodorous odor online detection and multi-process parameter analysis—a method for online detecting and analyzing multiple state parameters of fermentation and malodorous pollutant processes by using an electronic nose instrument of gas sensitivity and gas chromatography provided in the present disclosure.

FIG. 1 is a schematic diagram of technical routes such as a perception information fusion of a gas sensor array and a capillary gas chromatographic column, an electronic nose instrument development, an online multi-source detection of fermentation tail gases and malodorous odors a multi-process parameter analysis provided in the present disclosure. The technical route shown in FIG. 1 includes: (1) Evaluating and selecting performance of gas sensitive and gas chromatographic perception elements, in this route, the characteristic difference between a gas sensor and a capillary gas chromatographic column is deeply analyzed, so that the advantages of them two are complemented. (2) A technology route for modularizing a component such as a gas sensor array, in this route, structural modularization of important components such as a gas sensor array, a capillary gas chromatographic column, an automatic gas sampling, computer control and analysis is realized. (3) An online gas sensitive-gas chromatography perception model and information fusion technical route, in this route, a gas sensor response curve multi-information selection method satisfying the triangular stability principle and a semi-separation chromatogram multi-information selection method simulating a marathon game scene are provided, so that online perception and information fusion of the gas sensor array and the capillary gas chromatographic column are realized. (4) A technical route for establishing big odor data, in this technical route, big odor data X is formed on the basis of conventional offline instrument detection data such as electronic nose instrument with online multi-source gas sensitive/gas chromatographic perception data, professional laboratory smelling data, gas chromatography/mass spectrometry, spectrophotometry in a large number of bio-fermentation processes or malodorous pollution points. (5) Offline learning and online fine-tuning technical route of a machine learning model, and in this route, the machine learning model learns X offline to optimize and determine a model structure and multiple parameters; in a decision-making stage, the machine learning model learns the near-term responses of the gas sensitive/gas chromatography online to finely tune the parameter, determines the bio-fermentation process or the odor pollution type online according to a current perception vector $x(\tau)$ of the gas sensitivity/gas chromatography, and quantitatively predicts a concentration of main components of the fermentation liquors in the bio-fermentation processes or the concentrations of 8 components of malodorous pollutants specified by the Chinese national standard GB14554 and an OU value of the qualitative odor concentrations, so as to realize long-term online circulating detection and analysis of complex odors in multiple bio-fermentation processes and multiple malodorous pollution points.

Figure 2:
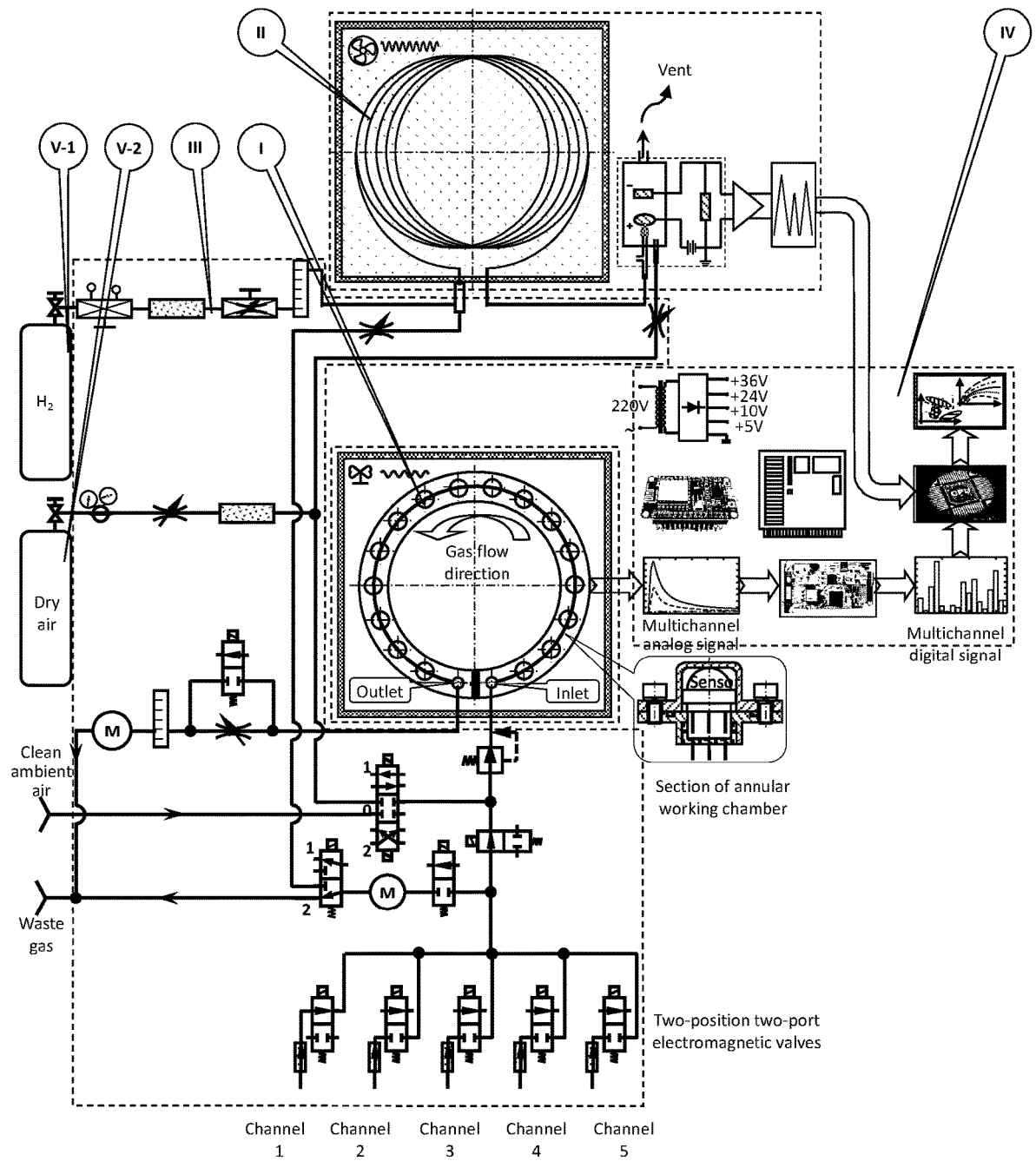
FIG. 2 is a schematic diagram of a working principle of an electronic nose instrument—a method for online detecting and analyzing multiple state parameters of fermentation and malodorous pollutant processes by using an electronic nose instrument of gas sensitivity and gas chromatography provided in the present disclosure.

FIG. 2 is a schematic diagram of a working principle of an electronic nose instrument by combining gas sensitivity and gas chromatography provided in the disclosure. The electronic nose instrument mainly includes a gas sensor array module I, a capillary gas chromatographic column module II, a gas auto-sampling module III, a computer control and analysis module IV, a hydrogen bottle V and a dry air bottle VI. $H_2$ is also used as a carrier gas and a fuel gas of a hydrogen flame ionization detector (FID) of the capillary gas chromatographic column module II; and dry air serves as combustion-supporting gas of the capillary gas chromatographic column module II on one hand and serves as calibration gas (not combusted) of the gas sensor array module I on the other hand.

Figure 3:
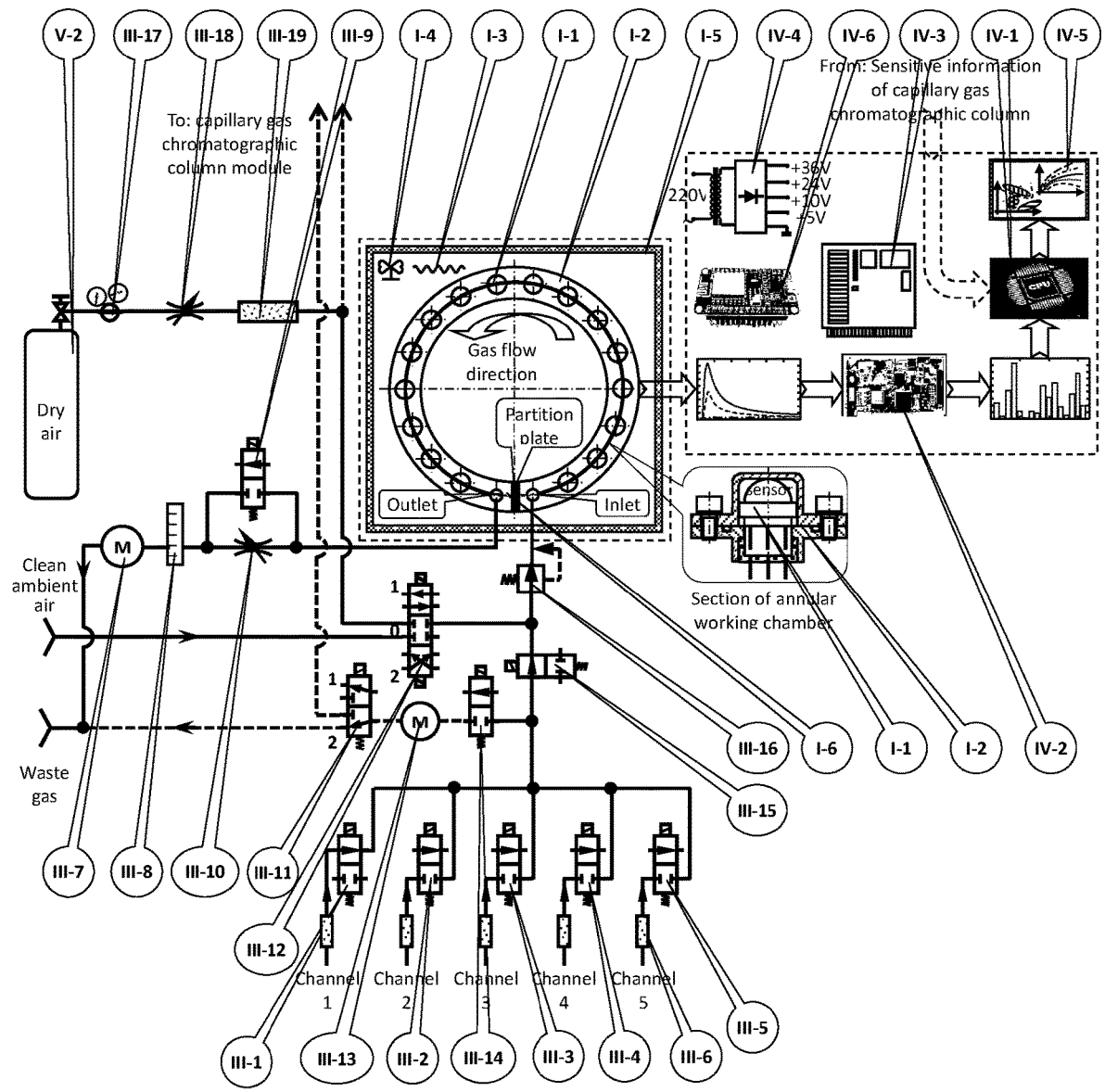
FIG. 3 is a schematic diagram of a working principle of a gas sensor array module and its gas circuit—a method for online detecting and analyzing multiple state parameters of fermentation and malodorous pollutant processes by using an electronic nose instrument of gas sensitivity and gas chromatography provided in the present disclosure.
Figure 4:
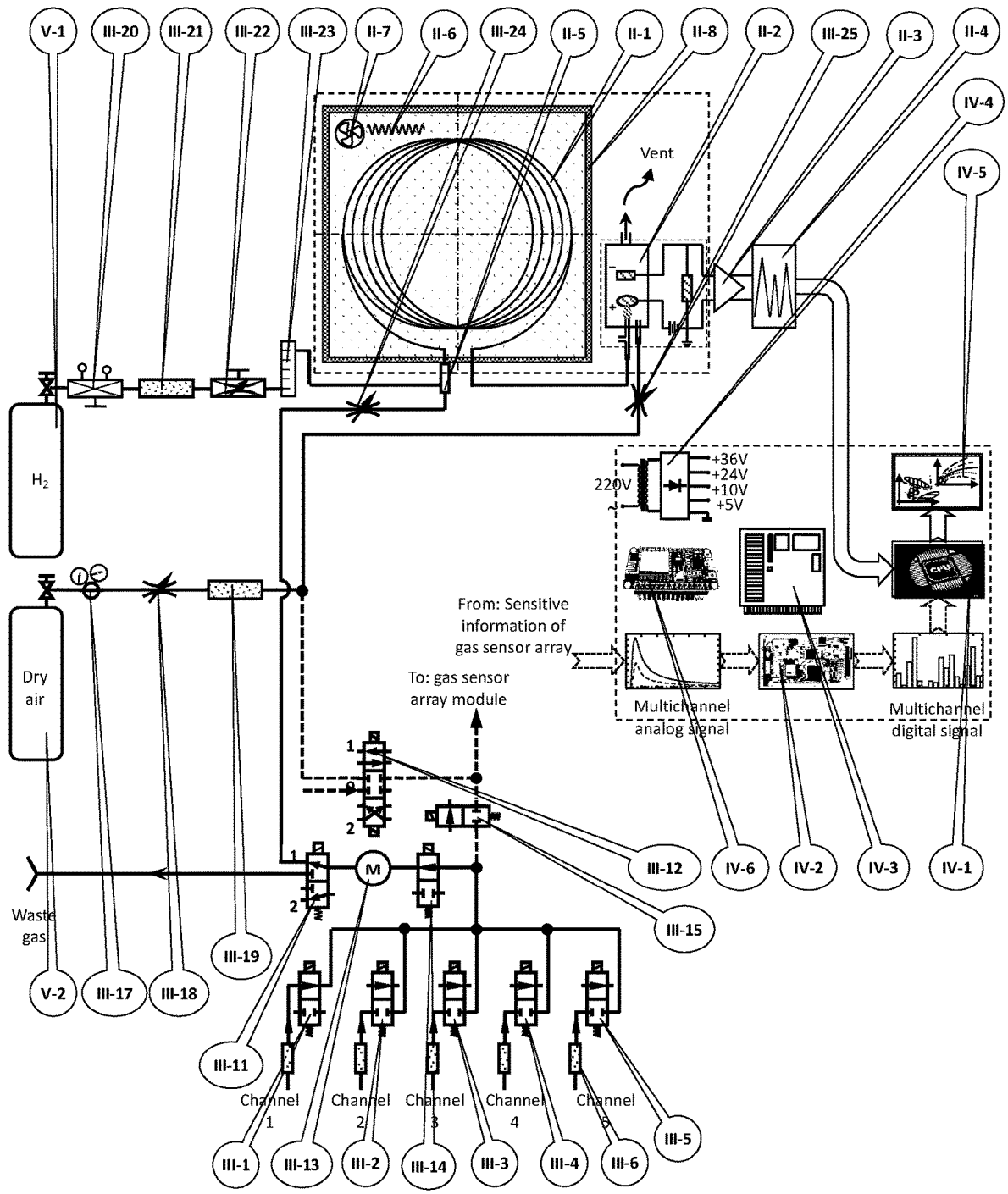
FIG. 4 is a schematic diagram of a working principle of a capillary gas chromatographic column module and its gas circuit—a method for online detecting and analyzing multiple state parameters of fermentation and malodorous pollutant processes by using an electronic nose instrument of gas sensitivity and gas chromatography provided in the present disclosure.

FIGS. 3 and 4 are two working principle diagrams of a gas sensor array module I, a capillary gas chromatographic column module II and a gas circuit of an electronic nose instrument provided in the present disclosure, respectively.

A main component units of the gas sensor array module I include a gas sensor array I-1, an annular working chamber I-2, a resistance heating element I-3, a fan I-4, a thermal insulation layer I-5 and a partition plate I-6, which are located in a middle right part of the electronic nose instrument. The capillary gas chromatographic column module II mainly includes a capillary gas chromatographic column II-1, a detector II-2, an amplifier II-3, a recorder II-4, a sampling inlet II-5, a resistance heating wire II-6, a fan II-7 and a thermal insulation layer II-8, which are located in the upper right part of the electronic nose instrument. The gas sensor array module I and the capillary gas chromatographic column module II are configured to convert chemical and physical information of odors into electric signals online.

A component units of the gas auto-sampling module III associated with the gas sensor array module I include: first to fifth two-position two-port electromagnetic valves III-1-III-5, a second two-position two-port electromagnetic valve III-2, a third two-position two-port electromagnetic valve III-3, a fourth two-position two-port electromagnetic valve III-4, a fifth two-position two-port electromagnetic valve III-5, a first purifier III-6, a first miniature vacuum pump III-7, a first flowmeter III-8, a sixth two-position two-port electromagnetic valve III-9, a first throttle valve III-10, a three-position four-port electromagnetic valve III-12, a seventh two-position two-port electromagnetic valve III-14, an eighth two-position two-port electromagnetic valve III-15, a pressure stabilizing valve III-16, a first pressure reducing valve III-17, a second throttle valve III-18 and a second purifier III-19.

A component units of the gas auto-sampling module III associated with the capillary gas chromatographic column module II include: a two-position three-port electromagnetic valve III-11, a second miniature vacuum pump III-13, a second pressure reducing valve III-20, a third purifier III-21, a third throttle valve III-22, a second flowmeter III-23, a fourth throttle valve III-24 and a fifth throttle valve III-25. The gas auto-sampling module III is located in a lower right part of the electronic nose instrument.

A main component units of the computer control and analysis module IV include: a computer mainboard IV-1, an A/D data acquisition card IV-2, a driving and control circuit board IV-3, a 4-path precision direct-current stabilized voltage power supply IV-4, a display IV-5 and a WIFI module IV-6, which are located in a left side of the electronic nose instrument. The WIFI module IV-6 is configured to transmit perception information of the gas sensor array module I and the capillary gas chromatographic column module II to a specified fixed/mobile terminal in real time.

Figure 5:
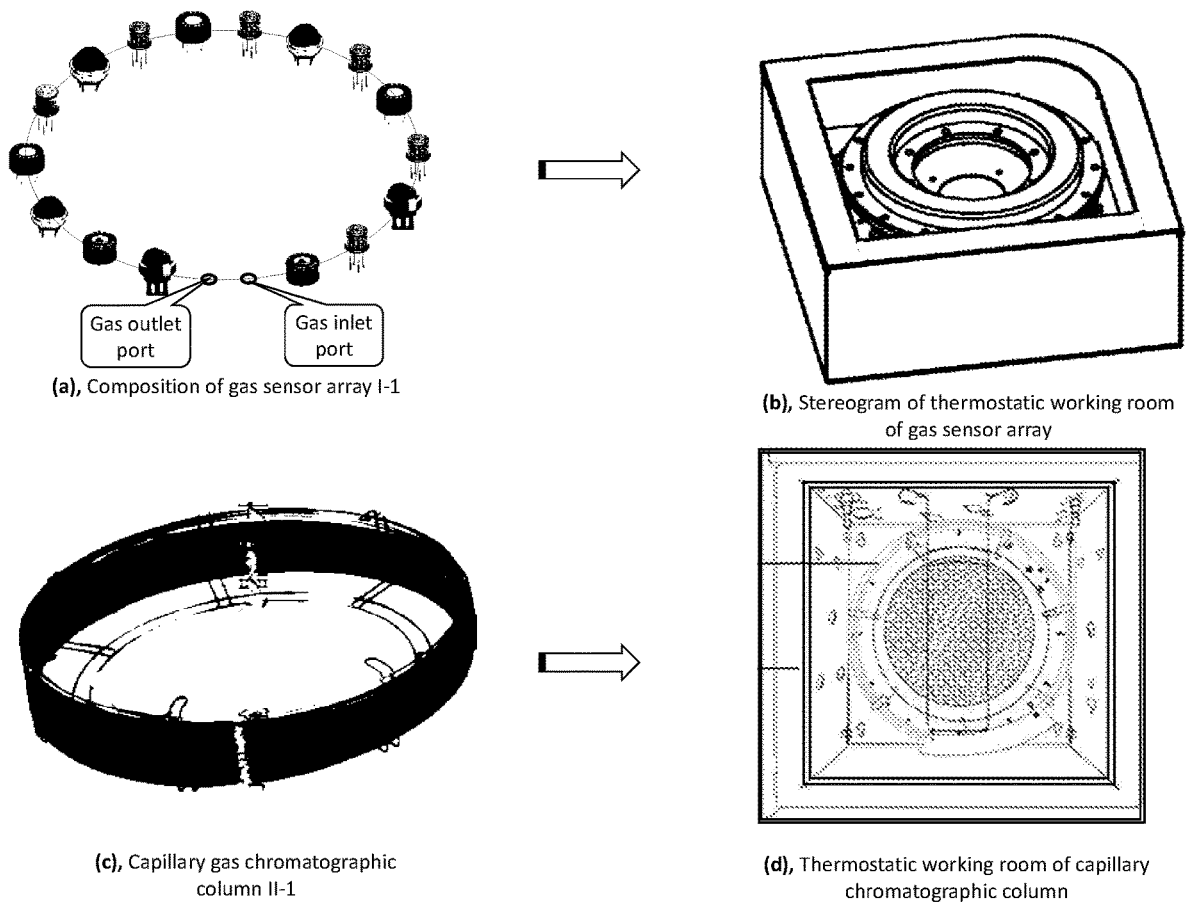
FIG. 5 is a schematic diagram of a gas sensor array module and a capillary gas chromatographic column module—a method for online detecting and analyzing multiple state parameters of fermentation and malodorous pollutant processes by using an electronic nose instrument of gas sensitivity and gas chromatography provided in the present disclosure.

FIG. 5 is a schematic diagram of a gas sensor array module I and a capillary gas chromatographic column module II of an electronic nose instrument. The gas sensor array and the capillary gas chromatographic column are located in two thermostatic boxes with different constant temperatures to form two modules which may be conveniently replaced according to the need.

Figure 6:
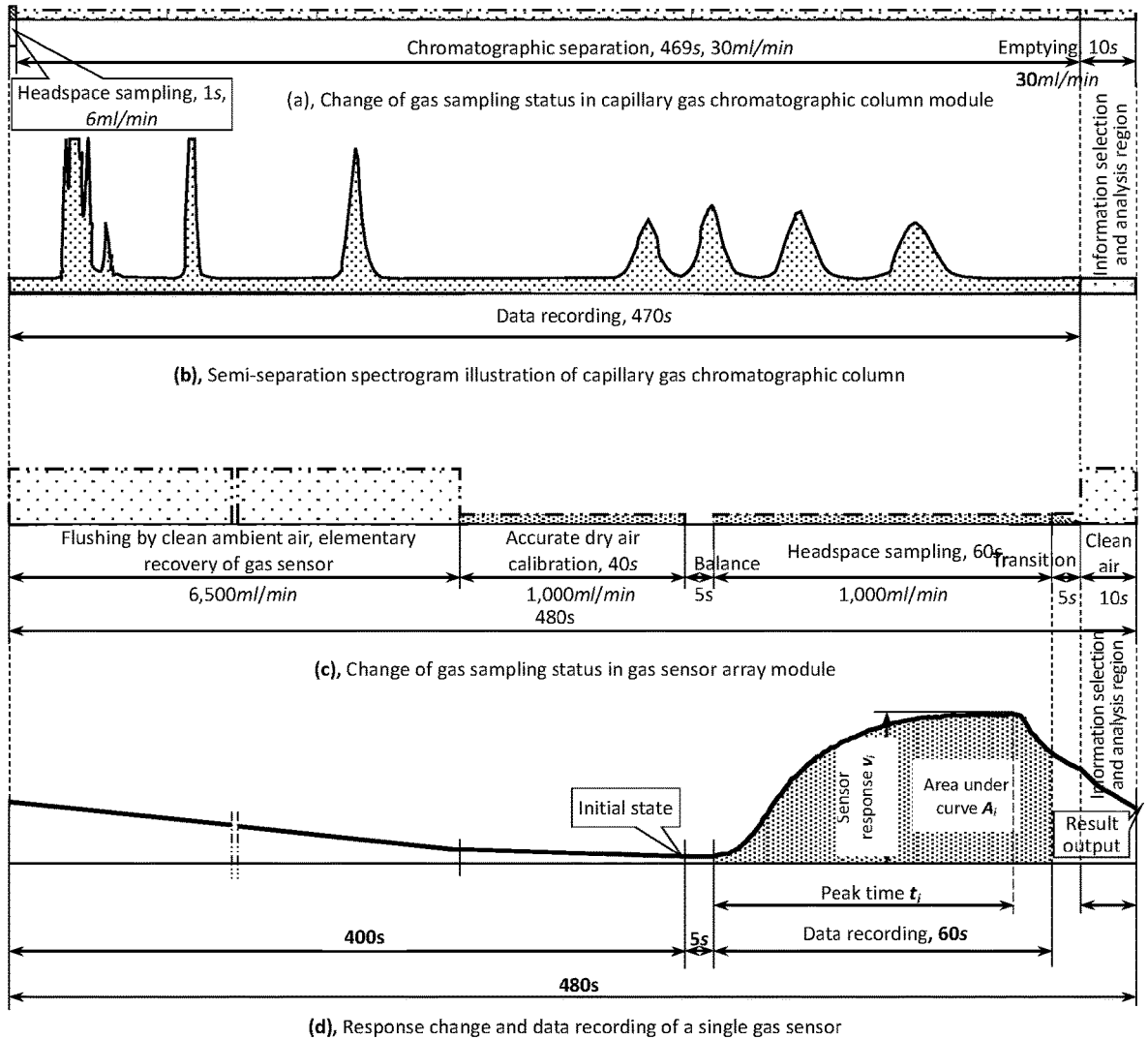
FIG. 6 is a schematic diagram of gas sampling time, a flow rate, and a gas sensor response change of a capillary gas chromatographic column and a gas sensitive array module in the single gas sampling period $T_0$=480 s—a method for online detecting and analyzing multiple state parameters of fermentation and malodorous pollutant processes by using an electronic nose instrument of gas sensitivity and gas chromatography provided in the present disclosure.

FIG. 6 is a schematic diagram of gas sampling time, a flow rate and a gas sensor response change condition of the gas sensor array module I and the capillary gas chromatographic column module II in the single gas sampling period $T_0=480$ s of the electronic nose instrument. The single gas sampling period may be adjusted between $T_0=5\text{-}10$ min, and FIG. 6 is exemplified by a default gas sampling period $T_0=480$ s. An adjustable time period is mainly a flushing stage by clean ambient air/rough recovery stage of the gas sensors in the gas sensor array module I and a separation stage of the capillary gas chromatographic column module II. FIG. 6 shows that in the single gas sampling period $T_0=480$ s, the gas sensor array module I and the capillary gas chromatographic column module II are not equal in sampling flow rates and accumulated sampling amount for a tested gas and are not synchronous in the sampling time points, but the information selection and analysis regions are performed simultaneously in the last 10 s time stage.

FIG. 6a shows a condition of the single gas sampling period of the capillary gas chromatographic column module II, and it includes three stages: (i) a headspace sampling stage of a tested gas, (ii) a chromatographic separation stage of the tested gas, (iii) chromatographic column emptying stage. (i) the headspace sampling stage of the tested gas is in the beginning of the single gas sampling period $T_0$, the sampling duration range is 0.5 s-1.5 s, is by default; the sampling flow rate range is 1.5 ml/min~15 ml/min, 6 ml/min by default; and the cumulative sampling volume range is 0.0125 ml~0.375 ml, 0.1 ml by default.

TABLE 1 the working parameters of the capillary gas chromatographic column module II and the on/off status of the relevant electromagnetic valves in a single gas sampling period $T_0 = 300\text{-}600$ s (480 s by default)

| Stage | Description | Duration (s) | Initial time-point (s) | Flow rate (ml/min) | Gas type | 2-position 3-port valve III-11 | 2-position 2-port valves III-1~III-5 | 3-position 4-port valve III-12 | 2-position 2-port valve III-14 | 2-position 2-port valve III-15 |
|---|---|---|---|---|---|---|---|---|---|---|
| (i) | gas sampling | 0.5-1.5 | 0 | 1.5~15 | tested gas | "1" | III-k on | "2" | on | off |
| (ii) | chromatographic separation | 289-589 | 1 | 30~50 | tested gas + H$_2$ | "2" | III-k on | "1"only 40 s | off | only on 60 s |
| (iii) | chromatographic column emptying | 10 | 290-590 | 30~50 | H$_2$ | "1" | III-(~k) on | "2" | on | off |

Referring to FIG. 6, in conjunction with FIG. 4, Table 1 gives the working parameters of the capillary gas chromatographic column module II and the on/off status of the relevant electromagnetic valves in the single gas sampling period $T_0=480$ s. In the headspace sampling stage of a tested gas (i), the two-position three-port electromagnetic valve III-11 is positioned at "1", the seventh two-position two-port electromagnetic valve III-14 is on, one of the first two-position two-port electromagnetic valve III-11 to the fifth two-position two-port electromagnetic valve III-5 is on, and the eighth two-position two-port electromagnetic valve III-15 is off. Supposed that the first two-position two-port electromagnetic valve III-1 is on, and at the moment, the tested gas in a bio-fermentation process (fermentation tank) or a malodorous pollution point, say a first monitoring point, sequentially flows through the first two-position two-port electromagnetic valve III-1, the seventh two-position two-port electromagnetic valve III-14, the two-position three-port electromagnetic valve III-11 and the fourth throttle valve III-24 under the suction action of the second miniature vacuum pump III-13, and then mixes with a carrier gas H$_2$ at the sampling inlet II-5, and thus flows into the capillary gas chromatographic column II-1.

In the headspace sampling stage of tested gas (i), if the default sampling flowrate is 6 ml/min and the default sampling duration is 1 s, then the sampling volume of the tested gas is 0.1 ml, which satisfies the optimal sampling amount requirement of the capillary gas chromatographic column. In the 369 s chromatographic separation stage of the tested gas (ii), in the $T_0=480$ s period, the two-position three-port electromagnetic valve III-11 is positioned at "2", and the seventh two-position two-port electromagnetic valve III-14 is off, namely the tested gas is cut off. During the period, under the pushing action of the carrier gas H$_2$, the components of the tested gas are separated apart in the capillary gas chromatographic column II-1.

In the chromatographic column emptying stage (iii) for the last 10 s of the single gas sampling period $T_0$, namely a cleaning and purging stage, the two-position three-port electromagnetic valve III-11 is positioned at "2", the seventh two-position two-port electromagnetic valve III-14 is on, one of the first two-position two-port electromagnetic valve III-1 to the fifth two-position two-port electromagnetic valve III-5 is on (but off when it is originally on), and the eighth two-port two-position electromagnetic valve III-15 is off. Supposed that the first two-position two-port electromagnetic valve III-1 is on, the sequential air flow through the first two-position two-port electromagnetic valve III-1, the seventh two-position two-port electromagnetic valve III-14 and the two-position three-port electromagnetic valve III-11 under the suction action of the second miniature vacuum pump III-13 and is then discharged to the outdoors. In this stage, the residues of the related pipelines in the current gas sampling period can be removed, and the preparation is made for the next gas sampling period. It should be noted that a position of the three-position four-port electromagnetic valve III-12 is determined by Table 2 given later.

Referring to FIG. 6, in conjunction with FIG. 3, Table 2 gives the working parameters of the gas sensor array module I and the on/off status of the relevant electromagnetic valves in the single gas sampling period $T_0$.

In the accurate calibration stage by dry air (ii), namely the 360 s-400 s time duration of the single gas sampling period $T_0$, the three-position four-port electromagnetic valve III-12 is positioned at "1", the sixth two-position two-port electromagnetic valve III-9, the seventh two-position two-port electromagnetic valve III-14 and the eighth two-position two-port electromagnetic valve III-15 are off, the dry air in the dry air bottle VI sequentially flows through, at a flow rate of 1,000 ml/min, the first pressure reducing valve III-17, the second throttle valve III-18, the second purifier III-19, the three-position four-port electromagnetic valve III-12, the pressure stabilizing valve III-16, the annular working chamber I-2, the gas sensor array I-1, the first throttle valve III-10 and the first flowmeter III-8, and finally is discharged to outdoor by lasting 40 s. During this stage, the gas sensor array I-1 accurately recovers to a reference state under the role of dry air. As the eighth two-position two-port electromagnetic valve III-15 is off, the on/off status of the first two-position two-port electromagnetic valve III-1 to the fifth two-position two-port electromagnetic valve III-5 do not affect the calibration of the gas sensor array I-1.

TABLE 2 the working parameters of the gas sensor array module I and the on/off status of the relevant electromagnetic valves in a single gas sampling period $T_0$ = 300-600 s (480 s by default).

| Stage | Description | Duration (s) | Initial time-point (s) | Flow rate (ml/min) | Gas type | 2-position 2-port valves III-1~III-5 | 2-position 2-port valve III-9 | 3-position 4-port valve III-12 | 2-position 2-port valve III-14 | 2-position 2-port valve III-15 |
|---|---|---|---|---|---|---|---|---|---|---|
| (i) | Rough recovery | 180-480 | 0 | 6,500 | Clean ambient air | III-k on only | On | Position '2' | On 0.5-1.5 s | Off |
| (ii) | Dry gas calibration | 40 | 180-480 | 1,000 | Dry air | III-k on only | Off | Position '1' | Off | Off |
| (iii) | Balance | 5 | 220-520 | 0 | — | III-k on only | Off | Position '0' | Off | Off |
| (iv) | Headspace sampling | 60 | 225-525 | 1,000 | Tested gas | III-k on only | Off | Position '0' | Off | On |
| (v) | Transition | 5 | 285-585 | 1,000 | Clean ambient air | III-(~k) on only | Off | Position '2' | On | Off |
| (vi) | Clean ambient air flushing | 10 | 290-590 | 6,500 | Clean ambient air | III-(~k) on only | On | Position '2' | On | Off |

Multiple main working states of the gas sensor array module I are elaborated in detail by using the single gas sampling period $T_0$=480 s as an example.

In the headspace sampling stage of a tested gas (iv), namely the 405 s-465 s duration by lasting 60 s in the single gas sampling period $T_0$, one of the first two-position two-port electromagnetic valve III-1 to the fifth two-position two-port electromagnetic valve III-5 is on only, the three-position four-port electromagnetic valve III-12 is positioned "0", and the sixth two-position two-port electromagnetic valve III-9 and the seventh two-position two-port electromagnetic valve III-14 are off, and the eighth two-position two-port electromagnetic valve III-15 is on. The tested gas in one of 5 bio-fermentation processes (fermentation tanks) or one of malodorous pollution points (such as a first monitoring point) sequentially flows through, at a flow rate of 1,000 ml/min, one of the first two-position two-port electromagnetic valve III-1 to the fifth two-position two-port electromagnetic valve III-5, the eighth two-position two-port electromagnetic valve III-15, the pressure stabilizing valve III-16, the annular working chamber I-2 and the gas sensor array I-1 in the annular working chamber I-2, the first throttle valve III-10, and the first flowmeter III-8 under the suction action of the first miniature vacuum pump III-7, and the tested gas is discharged to outdoor by lasting 60 s. During this time stage, the gas sensor array I-1 generates a sensitive response to the tested gas.

In the rough recovery stage of the gas sensors (i) and the flushing stage by clean ambient air (vi), namely two time durations of 0 s-360 s and 470 s-480 s lasting 370 s of the single gas sampling period $T_0$, the three-position four-port electromagnetic valve III-12 is 1 positioned at "2", the sixth two-position two-port electromagnetic valve III-9 is on, and the eighth two-position two-port electromagnetic valve III-15 is off, the clean ambient air sequentially flows through, at a flow rate of 6,500 ml/min, the three-position four-port electromagnetic valve III-12, the pressure stabilizing valve III-16, the annular working chamber I-2, the gas sensor array I-1 within the annular working chamber I-2, the sixth two-position two-port electromagnetic valve III-9 and the first flowmeter III-8, and finally is discharged to outdoor for 370 s. Under the role of the clean ambient air, the gas sensor array I-1 is elementarily recovered to a reference state. As the eighth two-position two-port electromagnetic valve III-15 is off, whether the first two-position two-port electromagnetic valve III-15 to the fifth two-position two-port electromagnetic valve III-5, the sixth two-position two-port electromagnetic valve III-9 and the seventh two-position two-port electromagnetic valve III-14 are on or off does not affect the rough recovery of the gas sensor array I-1.

It should be pointed out that "the clean ambient air" is the kind of the outdoor air at where the electronic nose instrument is located by the dust removal, dehumidification and aseptic pretreatments, and is only used for the rough recovery of the gas sensor array I-1, flushing the inner walls of the annular working chamber I-2 as well as the related pipelines, and taking away the accumulated heat volume generated by the gas sensor array I-1.

Referring to FIG. 6, the gas sensor array module I and the capillary gas chromatographic column module II simultaneously enter the information selection and analysis region during the last 10 s of the single gas sampling period $T_0$. The computer control and analysis module IV selects 3 pieces of perception information for each gas sensor, i.e., a steady-state peak value $v_{gsi}(\tau)$, a peak time $t_{gsi}(\tau)$ corresponding to $v_{gsi}(\tau)$ and an area under the curve $A_{gsi}(\tau)$ from each voltage response curve of the gas sensor obtained in an interval of $[T_0-75 \text{ s}, T_0-15 \text{ s}]$; selects 21 pieces of chromatographic perception curve, i.e., the first 10 maximum chromatographic peak values $v_{gcj}(\tau)$, the retention time $t_{gcj}(\tau)$ corresponding to the first 10 maximum chromatographic peak values, and the area $A_{gc}(\tau)$ under the chromatogram curve in the time stage of $[0, T_0-10 \text{ s}]$. The method is a basis for analyzing and predicting either a bio-fermentation process or the malodorous pollution region by the electronic nose instrument, and is a basis for establishing big odor data X; and the machine learning model in the computer control and analysis module IV is configured to identify odor types and quantitatively predict its intensity and main concentration index values according to the perception vector $x(\tau)$.

Figure 7:
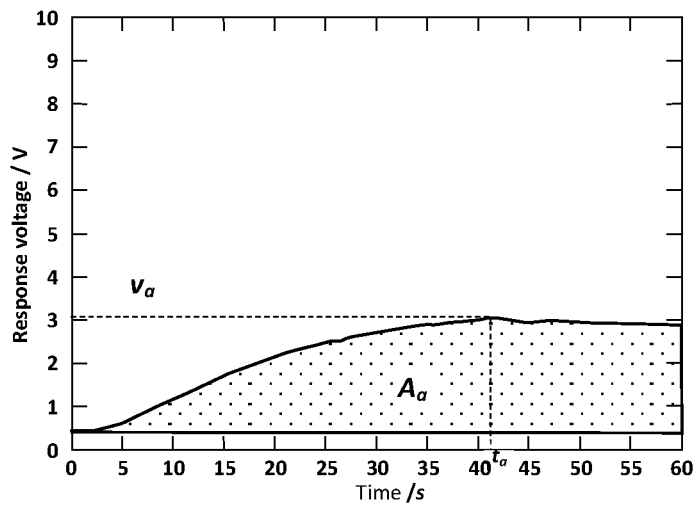
FIG. 7 is a schematic diagram of multi-information selection of a gas sensor response curve in the single gas sampling period $T_0$=480 s—a method for online detecting and analyzing multiple state parameters of fermentation and malodorous pollutant processes by using an electronic nose instrument of gas sensitivity and gas chromatography provided in the present disclosure.
Figure 7:
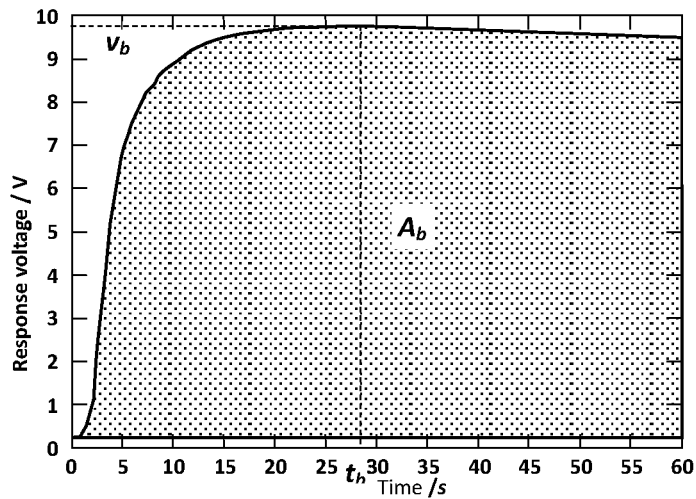
Figure 7:
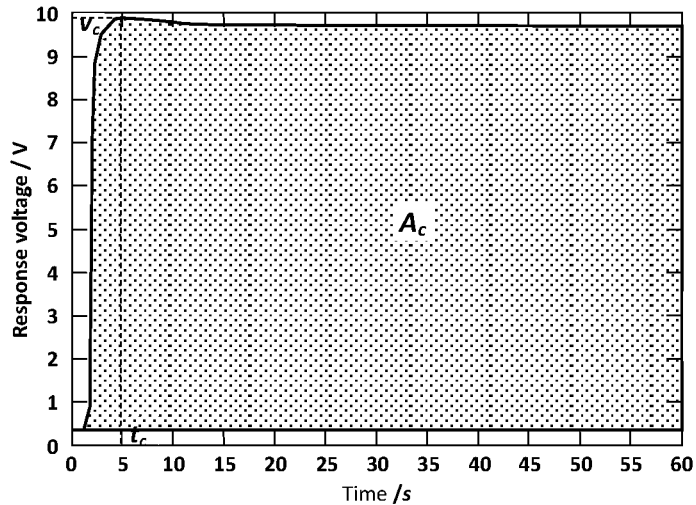

FIG. 7 is a multi-feature selection diagram in a response curve of a gas sensor in the single gas sampling period $T_0=480$ s. An example of the corresponding curves of 3 gas sensors TGS822, TGS826 and TGS832 for a petroleum wax sample, 2,000 ppm ethylene gas and 5,000 ppm ethanol vapor, respectively, is shown. The steady-state maximum values of the voltage response curves of the two graphs of FIG. 7b and FIG. 7c are equal, i.e., $v_b=v_c$. If only according to a conventional single steady-state maximum voltage value selection method in a response curve, the 2,000 ppm ethylene gas and the 5,000 ppm ethanol vapor cannot be distinguished by the electronic nose instrument at the moment. By a careful observation, we have found that following three situations are shown in both FIG. 7b and FIG. 7c. In the situation 1, although the steady-state maximum values in the voltage response curves are equal, the peak time points corresponding to the peak values are not equal, and the areas under the curve are also unequal. The situation 2 is that the peak time points are equal, but the peak values and the areas under the curves are unequal. The situation 3 is that the areas under the curves are equal, but the peak time points and the peak values are unequal.

According to FIG. 7, the present disclosure proposes that: a steady-state maximum value $v_{gsi}(\tau)$ of the voltage response, peak time point $t_{gsi}(\tau)$ beginning at the headspace sampling of the tested gas and corresponding to the steady-state maximum value $v_{gsi}(\tau)$, and an area $A_{gsi}(\tau)$ under the response curve for the headspace sampling of the tested gas lasting 60 s are selected from a response curve of one gas sensor i (i=1,2, . . . , 16). If the gas sensor array is composed of 16 sensitive elements, then an information selection and processing stage takes 10 s in the single gas sampling period $T_0$, the computer control and analysis module IV sequentially selects 3×16=48 feature values from 16 response curves as the primary sensitive information of the gas sensor array module I for the tested gas, which is recorded as $x_{gs}(\tau)=\{(v_{gs1}(\tau), v_{gs2}(\tau), \ldots, v_{gs16}(\tau)); (t_{gs1}(\tau), t_{gs2}(\tau), \ldots, t_{gs16}(\tau)); (A_{gc1}(\tau), A_{gc2}(\tau), \ldots, A_{gc16}(\tau))\}$.

Figure 8:
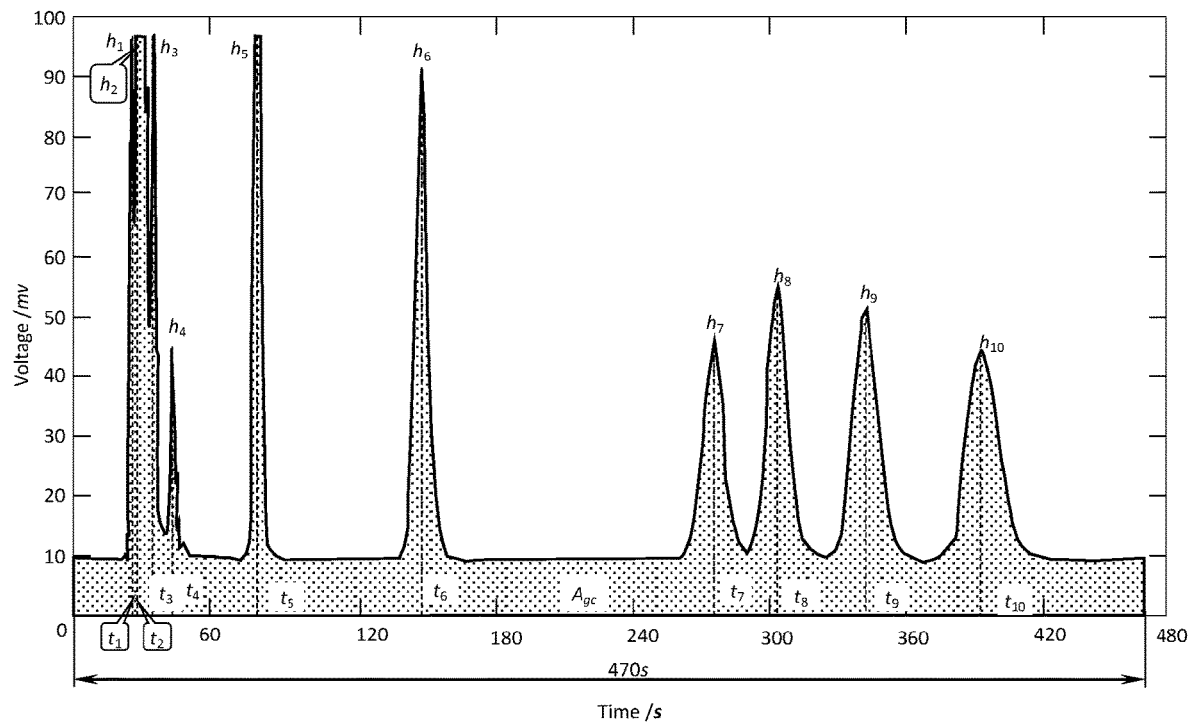
FIG. 8 is a schematic diagram of multi-information selection of a semi-separation chromatogram in the single gas sampling period $T_0$=480 s—a method for online detecting and analyzing multiple state parameters of fermentation and malodorous pollutant processes by using an electronic nose instrument of gas sensitivity and gas chromatography provided in the present disclosure.

FIG. 8 is an information selection diagram of a semi-separation chromatogram in the single gas sampling period $T_0=480$ s. In an 5 s information selection region within the single gas sampling period $T_0$, the computer control and analysis module IV sequentially selects 21 feature values, including 10 groups of peak heights and retention time points $\{h_{gcj}(\tau), t_{gcj}(\tau)\}$ (j=1, 2, . . . , 10) and an area $A_{gc}(\tau)$ under a semi-separation spectrogram curve with a specified duration 470 s as the primary perception information pieces of the capillary gas chromatographic column module II to the tested gas, which is recorded as $x_{gc}(\tau)=\{(h_{gc1}(\tau), h_{gc2}(\tau), \ldots, h_{gc10}(\tau)); (t_{gc1}(\tau), t_{gc2}(\tau), \ldots, t_{gc10}(\tau)); A_{gc}(\tau)\}$.

Figure 9:
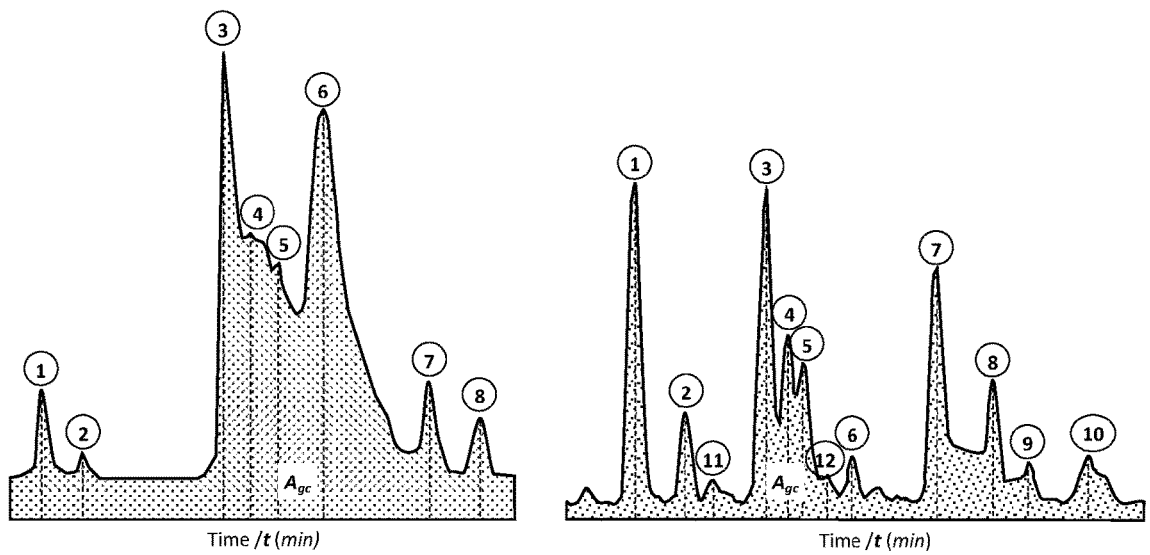
FIG. 9 is a schematic diagram of multi-information selection of a semi-separation chromatogram when a number of chromatographic peaks is less than or greater than 10 in the single gas sampling period $T_0$=480 s—a method for online detecting and analyzing multiple state parameters of fermentation and malodorous pollutant processes by using an electronic nose instrument of gas sensitivity and gas chromatography provided in the present disclosure.

FIG. 9 is a feature selection diagram of two semi-separation chromatograms in the single gas sampling period $T_0=480$ s. The semi-separation chromatogram in FIG. 9a has only 8 chromatographic peaks, whereby only 8 peak values $h_{gc\_i}(\tau)$ (i=1,2, . . . , 8) and 8 corresponding retention time points $t_{gcj}(\tau)$ (i=1,2, . . . , 8), and an area $A_{gc}(\tau)$ under the curve of the semi-separation chromatogram are obtained. Our action is that the insufficient chromatographic peak values and corresponding retention time points less than 10 in quantities are zero-filling. Therefore, in FIG. 9a, the resulting chromatogram perception information is $x_{gc}(\tau)=\{(h_{gc1}(\tau), h_{gc2}(\tau), \ldots, h_{gc8}(\tau), 0, 0); (t_{gc1}(\tau), t_{gc2}(\tau), \ldots, t_{gc8}(\tau), 0, 0); A_{gc}(\tau)\}$. Because the semi-separation chromatogram in FIG. 9b has more than 10 chromatographic peaks, the top 10 maximum chromatographic peaks from them accordingly.

In the present disclosure, the semi-separation chromatogram is regarded as a part of the perception information or mode of the electronic nose instrument, and the big odor data is established by combining the perception information of the gas sensor array, and the unknown odor recognition, qualitative analysis and main component quantitative prediction are realized by means of an artificial intelligence machine learning method. In the information selection and processing region of the single gas sampling period $T_0$ lasting for 10 s, the computer control and analysis module IV fuses the perception information by the gas sensor array module I and the capillary gas chromatographic column module II for the tested gas in different time intervals, performs the normalized preprocessing, and thus obtains a perception information vector by the electronic nose instrument for one tested gas sample, that is, $x(\tau)=x_{gs}(\tau)+x_{gc}(\tau)=\{(v_{gs1}(\tau), v_{gs2}(\tau), \ldots, v_{gs16}(\tau)); (t_{gs1}(\tau), t_{gs2}(\tau), \ldots, t_{gs16}(\tau)); (A_{gc1}(\tau), A_{gc2}(\tau), \ldots, A_{gc16}(\tau)); (h_{gc1}(\tau), h_{gc2}(\tau), \ldots, h_{gc10}(\tau)); (t_{gc1}(\tau), t_{gc2}(\tau), \ldots, t_{gc10}(\tau)); A_{gc}\} \in R^{69}$. The perception vector $x(\tau) \in R^{69}$ is the basis of the electronic nose instrument for online odor style identification and quantitative prediction of main component concentrations for a specified bio-fermentation process or malodorous pollution point.

Figure 10:
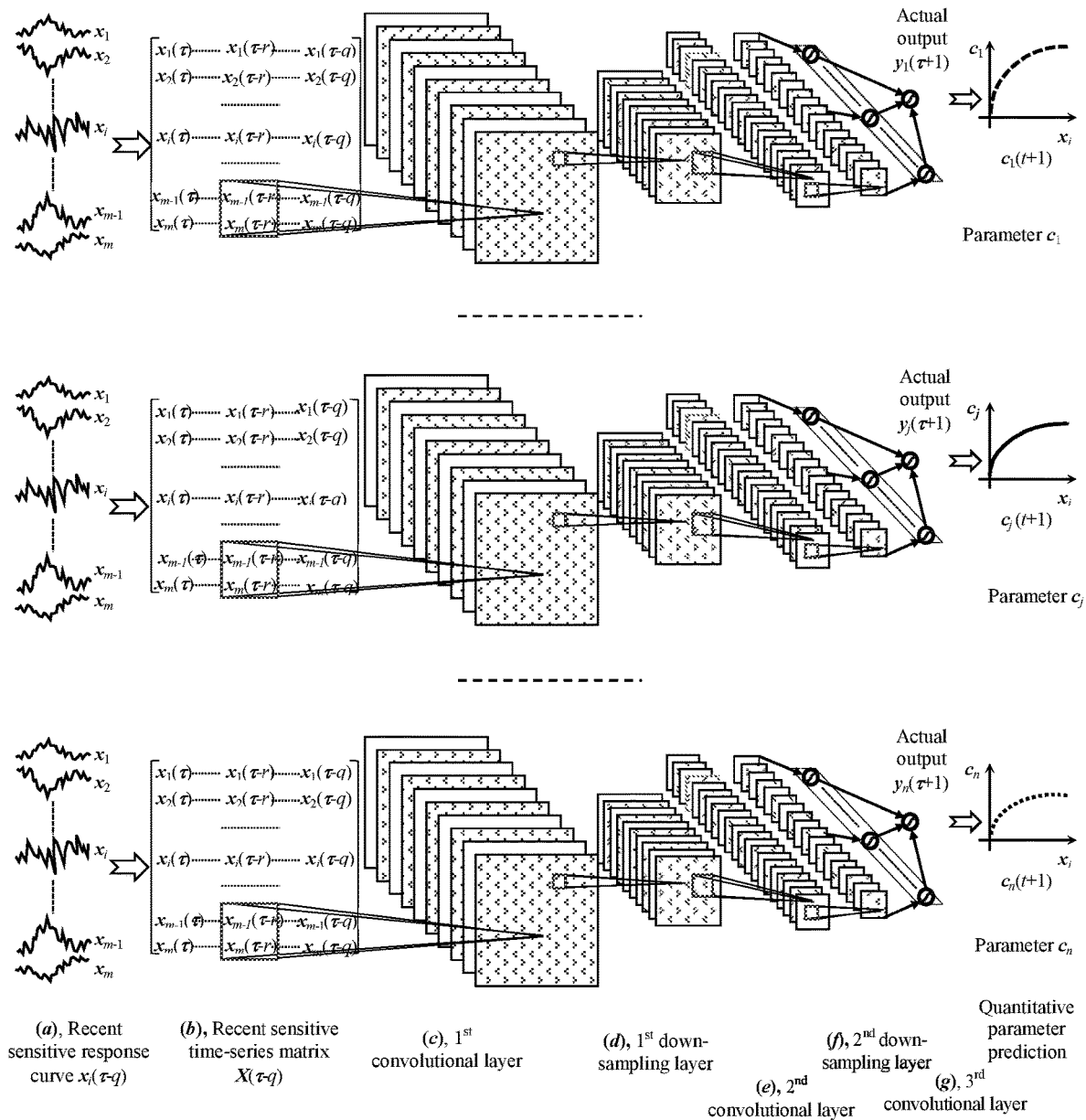
FIG. 10 is a schematic diagram of online quantitative prediction of multi-parameter "divide-and-conquer" of a modular deep convolutional neural network model—a method for online detecting and analyzing multiple state parameters of fermentation and malodorous pollutant processes by using an electronic nose instrument of gas sensitivity and gas chromatography provided in the present disclosure.

FIG. 10 is a schematic diagram of multi-parameter "divide-and-conquer" quantitative prediction of a deep convolutional neural network model of machine learning with an "online continuous" analysis mode. The method includes the following specified steps: according to a time-series matrix $X(\tau-q)$ recently sensed by the gas sensor array module I and the capillary gas chromatographic column module II, the types of fermentation and malodorous pollution, the odor intensity and the main components concentration values are predicted one by one through multiple single-output deep convolution neural networks. Here, r is the current time, q is the recently elapsed time, and $\tau-q$ is the recent interval. Thus, the dimensionality of the time-series matrix $X(\tau-q)$ is $R^{69\times(\tau-q+1)}$. The value of q is generally appropriate for about 6 hours in a current fermentation or malodorous pollution process.

To determine the structure and parameters of a modular convolutional neural network model, big odor data needs to be established, which includes: online perception data of the gas sensor array module I and the capillary gas chromatographic column module II for a large number of bio-fermentation processes and malodorous pollution regions; offline monitoring data of conventional instruments such as a gas chromatography, a mass spectrometer and a spectrophotometer; tag data of known types and constituents of odors; and sensory assessment data.

The next step is the fusion of the perception data of the gas sensor array I-1 and of the capillary gas chromatographic column II-1, including normalization and dimensionality reduction pretreatment. To reduce the difficulty of big odor data analysis, a "divide-and-conquer" strategy is adopted to decompose a complex multi-odor qualitative and quantitative analysis problem, namely a complex multi-odor type identification problem and a complex multi-odor intensity and composition quantitative estimation problem, into multiple one-to-one identification and multiple simple-component intensity and one-to-one quantitative prediction of important compositions, namely to decompose an n-curve/n-curved-surface fitting problem from an overall n-curve/n-curved-surface fitting problem, and the one-to-one n-curve/n-curved-surface fitting problem is solved by n single-output deep convolutional neural network models, each for one.

According to the present disclosure, multiple modular single-output deep convolutional neural networks are adopted to realize online multi-parameter quantitative prediction, each for one. A single-output deep convolutional neural network includes 1 input layer, 3 convolutional layers, 2 down-sampling layers and 1 output unit, which mainly learns the data with labels and data with known components in the big odor data. The activation functions of each hidden layer and the output layer are the corrected Sigmoid activation functions $f(\varphi)=3(1+\exp(-\varphi/3))^{-1}$, and an offline error back-propagation layer-by-layer learning algorithm is adopted. The scan window size of convolutional layer may be 5×5, and the overlap scan step size may be 1. The convolutional kernels are a combination of a sine kernel, a cosine kernel, a polynomial kernel, a Gaussian kernel, a Sigmoid kernel, a wavelet kernel, and a Laplace kernel. The scan windows in the down-sampling layers may have a size of 2×2 without overlap, i.e., a step size of 2, with maximum, mean, and mean squared error features extracted from each scan window. In the decision-making stage, n single-output deep convolutional neural network models predict multiple quantitative index values of in the $\tau+1$, $\tau+2$, $\tau+3$ and other time points according to a recent gas sensitive/gas chromatography perception time-series matrix $X(\tau-q)$, and the quantitative index values include odor types, intensity and concentration values of main components.

The specified components of the recent gas sensitive/gas chromatography perception time-series matrix $X(\tau-q)$ are:

$$X(\tau-q) = \begin{bmatrix} x_1(\tau) & x_1(\tau-1) & \ldots & x_1(\tau-r) & \ldots & x_1(\tau-q) \\ x_2(\tau) & x_2(\tau-1) & \ldots & x_2(\tau-r) & \ldots & x_2(\tau-q) \\ \ldots & \ldots & \ldots & \ldots & \ldots & \ldots \\ x_i(\tau) & x_i(\tau-1) & \ldots & x_i(\tau-r) & \ldots & x_i(\tau-q) \\ \ldots & \ldots & \ldots & \ldots & \ldots & \ldots \\ x_{m-1}(\tau) & x_{m-1}(\tau) & \ldots & x_{m-1}(\tau-r) & \ldots & x_{m-1}(\tau-q) \\ x_m(\tau) & x_m(\tau) & \ldots & x_m(\tau-r) & \ldots & x_m(\tau-q) \end{bmatrix} \in R^{m \times q} \quad (1)$$

In the present disclosure, m=69 and q=9.

When only one point is detected, that is, a cyclical gas sampling period T is equal to a single gas sampling period $T_0$=8 min, the setting of "q=9" is equivalent to a time-series perception response matrix by using a gas sensitivity/gas chromatography according to in the time period from the current moment r to the past 1.2 hours, and is equivalent to the prediction of possible changes of odor intensity and main components in the future 8 min, 16 min and 24 min according to the change of fermentation or malodorous pollution processes in the past 1.2 hour period. When 5 points are detected, i.e., the cyclical gas sampling period is $T=5T_0$=40 min, and the setting of "q=9" is equivalent to the prediction of possible changes of odor intensity and main components in the coming 40 min, 80 min and 120 min according to a time-series response matrix by using a gas sensitivity/gas chromatographic perception in the time interval from the current moment z to the past 6 hours.

The invention claimed is:

1. A method for online detecting and analyzing a plurality of state parameters in fermentation and malodorous pollution processes by using an electronic nose instrument of gas sensitivity and gas chromatography, wherein the electronic nose instrument comprises a gas sensor array module I, a capillary gas chromatographic column module II, a gas auto-sampling module III, a computer control and analysis module IV and an auxiliary gas source V, which is configured to perform cyclically long-term online detection and intelligent analysis of a plurality of bio-fermentation processes or a plurality of malodorous pollution processes, wherein, the gas sensor array module I comprises a gas sensor array I-1, an annular working chamber I-2 for installing the gas sensor array I-1, a resistance heating element I-3, a fan I-4, a thermal insulation layer I-5 and a partition plate I-6 and is located in a middle right side of the electronic nose instrument;

the capillary gas chromatographic column module II comprises a capillary gas chromatographic column II-1, a detector II-2, an amplifier II-3, a recorder II-4, a sampling inlet II-5, a resistive heating wire II-6, a fan II-7 and a thermal insulation layer II-8 and is located in an upper right side of the electronic nose instrument;

the gas auto-sampling module III comprises a first two-position two-port electromagnetic valve III-1, a second two-position two-port electromagnetic valve III-2, a third two-position two-port electromagnetic valve III-3, a fourth two-position two-port electromagnetic valve III-4, a fifth two-position two-port electromagnetic valve III-5, 5 first purifiers III-6, a first miniature vacuum pump III-7, a first flowmeter III-8, a sixth two-position two-port electromagnetic valve III-9, a first throttle valve III-10, a two-position three-port electromagnetic valve III-11, a three-position four-port electromagnetic valve III-12, a second miniature vacuum pump III-13, a seventh two-position two-port electromagnetic valve III-14, an eighth two-position two-port electromagnetic valve III-15, a pressure stabilizing valve III-16, a first pressure reducing valve III-17, a second throttle valve III-18, a second purifier III-19, a second pressure reducing valve III-20, a third purifier III-21, a third throttle valve III-22, a second flowmeter III-23, a fourth throttle valve III-24 and a fifth throttle valve III-25 and is located in a lower right side of the electronic nose instrument; and the computer control and analysis module IV comprises a computer mainboard IV-1, an A/D data acquisition card IV-2, a driving and control circuit board IV-3, a 4-path precision direct-current stabilized voltage power supply IV-4, a display IV-5 and a WIFI module IV-6 and is located in a left side of the electronic nose instrument;

wherein one bio-fermentation process or one malodorous pollution point is referred to as one monitoring point; a single gas sampling period of the electronic nose instrument at one monitoring point is $T_0$–300-600s, and is $T_0$=480s by default; in the single gas sampling period $T_0$, respectively sucking, by the first miniature vacuum pump III-7 and the second miniature vacuum pump III-13, a tested gas at one monitoring point into the gas sensor array module I and the capillary gas chromatographic column module II; generating, by the gas sensor array I-1 and the capillary gas chromatographic column II-1, a sensitive response; and obtaining, by the electronic nose instrument, a group of response curves of the gas sensor array and a gas chromatogram, which is a gas sensitivity/gas chromatography simulation signal obtained by perceiving a tested gas sample using the electronic nose instrument;

in the single gas sampling period $T_0$, selecting, by the computer control and analysis module IV, 3 perception information from each voltage response curve with a duration of 60s of the gas sensor array I-1 to satisfy a triangular stability principle and improve the qualitative and quantitative capacity of the gas sensor array, wherein the 3 perception information comprises a steady-state peak value $V_{gsi}(\tau)$, peak time $t_{gsi}(\tau)$ corresponding to the $V_{gsi}(\tau)$, and an area $A_{gsi}(\tau)$ under the voltage response curve; in a case where the gas sensor array I-1 comprises 16 gas sensors, i=1,2, . . . ,16, obtaining, by the computer control and analysis module IV, 16*3=48 perception component in total from 16 response curves of the gas sensor array in the single gas sampling period $T_0$;

in the single gas sampling period $T_0$, in a case where the electronic nose instrument does not pursue a complete between-peak separation of a gas chromatogram, selecting, by the computer control and analysis module IV, 21 perception component from a semi-separation gas chromatogram to improve the online detection capability of the gas chromatographic column, wherein the 21 perception components comprise first 10 maximum chromatographic peak values $h_{gcj}(\tau)$, 10 retention time $t_{gcj}(\tau)$ corresponding to the first 10 maximum chromatographic peak values, and an area $A_{gc}(\tau)$ under a whole chromatogram curve;

in the single gas sampling period $T_0$, perceiving, by the electronic nose instrument, tested gas in one bio-fermentation process or at one malodor pollution point; and fusing, by the computer control and analysis module IV, 48 perception components extracted from the 16 response curves of the gas sensor array I-1 and 21 perception components extracted from the semi-separation chromatogram of the capillary gas chromatographic column II-1 to obtain a perception vector $x(\tau) \in R^{69}$ with m=48+21=69 dimensions, wherein the perception vector $x(\tau) \in R^{69}$ is referred to as a sample; and using as a basis of doing a qualitative and quantitative analysis on a bio-fermentation process or a malodorous pollution process by the electronic nose instrument;

setting, by the electronic nose instrument, a cyclical gas sampling period for n ($\leq$5) bio-fermentation processes or n ($\leq$5) malodorous monitoring points to be $T=nT_0$; obtaining, by the electronic nose instrument, n samples in sequence, storing them in n data files of a computer hard disk corresponding to the n samples respectively, and then sending sample data to a cloud terminal and a specifically fixed/mobile terminal through the WIFI routing module; wherein in a case of $T_0$=480s, the cyclical tested gas sampling period is $T=nT_0=n*480s$, which is equivalent to detect once in every other n*480s for one fermentation tank or one malodorous pollution point being detected every n*480s;

forming, by the electronic nose instrument, a main body of big odor data X through a long-term online detection of the plurality of bio-fermentation processes and a plurality of malodorous pollution points over years; wherein the data set X further comprises offline detection data of a gas chromatography instrument, a mass spectrometry instrument and a spectrophotometric instrument, odor unit (OU) concentration data obtained through laboratory sensory smelling, and bio-fermentation type data of penicillin, erythromycin, vinegar, soy sauce, cooking wine and monosodium glutamate recorded by on-site operators, and malodorous pollution monitoring region type data of a chemical industrial park, a refuse landfill, a sewage treatment plant and a livestock and poultry farm; establishing, by a part of subsets of the data set X, a corresponding relationship between a response vector of gas sensor array and gas chromatography and a plurality of bio-fermentation processes/malodorous pollution types comprising many component concentrations; and in the learning stage, making each perception component of the big odor data X to be normalize, offline learning, by a machine learning model of the computer control and analysis module IV, the big odor data X to determine the structure and parameters of the machine learning model; in the decision-making stage, online learning, by the machine learning model, a group of recent response patterns of gas sensor array and gas chromatography to finely tune the parameters of the machine learning model, online determining the types of the plurality of bio-fermentation processes and malodorous pollutions, and quantitatively predicting the concentrations of main chemical compositions of fermentation liquids during the bio-fermentation processes or 8+1 concentration index values of malodorous pollutants, comprising 8 specified chemical components, ammonia ($NH_3$), hydrogen sulfide ($H_2S$), carbon disulfide ($CS_2$), trimethylamine ($C_3H_9N$), methyl mercaptan ($CH_4S$), methyl sulfide ($C_2H_6S$), dimethyl disulfide ($C_2H_6S_2$) and styrene ($C_8H_8$) specified by the Chinese national standard GB14554, as well as an OU concentration value, by depending upon a group of time-serial response patterns of gas sensor array and gas chromatography.

2. The method for online detecting and analyzing a plurality of state parameters in fermentation and malodorous pollution processes by using an electronic nose instrument of gas sensitivity and gas chromatography of claim 1, wherein the gas sensor array I-1 and the annular working chamber I-2 are located in a thermostatic box with a temperature of 55±0.1° C.; in the single gas sampling period $T_0$, making the gas sensor array module I be sequentially subject to 6 stages, i.e., an rough recovery stage of the gas sensor array I-1 for $T_0$-120s, an accurate calibration stage by dry air for 40s, a balance stage for 5s, a headspace sampling stage of tested gas for 60s, a transition stage for 5s and a flushing stage by clean ambient air for 10s; wherein gas types and flow rates for these 6 stages are in order: (i) clean ambient air of 6,500 ml/min; (ii) dry air of 1,000 ml/min; (iii) no gas flow; (iv) tested gas of 1,000 ml/min; (v) clean ambient air of 1,000 ml/min; (vi) clean ambient air of 6,500 ml/min; where "transition" mainly refers to a change from the tested gas to the clean ambient air.

3. The method for online detecting and analyzing a plurality of state parameters in fermentation and malodorous pollution processes by using an electronic nose instrument of gas sensitivity and gas chromatography of claim 1, wherein an interval of $[T_0-75s, T_0-15s]$ in the single gas sampling period $T_0$ is the headspace sampling stage of the gas sensor array module I for the tested gas, setting one two-position two-port electromagnetic valve III-k (k=1, 2, . . . ,5) among the first two-position two-port electromagnetic valve III-1 to the fifth two-position two-port electromagnetic valve III-5 to be on, setting the three-position four-port electromagnetic valve III-12 to be "0", setting the sixth two-position two-port electromagnetic valve III-9 to be off, setting the seventh two-position two-port electromagnetic valve III-14 to be off, and setting the eighth two-position two-port electromagnetic valve III-15 to be on; and under the suction action of the first miniature vacuum pump III-7, making a tested gas at one monitoring point sequentially flow through, at a flow rate of 1,000 ml/min, the $k^{th}$ two-position two-port electromagnetic valve III-k (k=1, 2, . . . ,5), the eighth two-position two-port electromagnetic valve III-15, the pressure stabilizing valve III-16, the annular working chamber I-2, the gas sensor array I-1, the first throttle valve III-10 and the first flowmeter III-8, and finally, discharging the tested gas outdoors and lasting for 60s, and therefore, generating, by the gas sensor array I-1, a sensitive response to the tested gas, and storing the sensitive response in a temporary file of the computer control and analysis module IV.

4. The method for online detecting and analyzing a plurality of state parameters in fermentation and malodorous pollution processes by using an electronic nose instrument of gas sensitivity and gas chromatography of claim 1, wherein an interval of $[T_0-120s, T_0-80s]$ of the single gas sampling period $T_0$ is the accurate calibration stage of the gas sensor array module I by the dry air, setting the three-position four-port electromagnetic valve III-12 to be "1", setting the sixth two-position two-port electromagnetic valve III-9, the seventh two-position two-port electromagnetic valve III-14, and the eighth two-position two-port electromagnetic valve III-15 to be off; and making dry air in the dry air bottle V-2 sequentially flow through, at a flow rate of 1,000 ml/min, the first pressure reducing valve III-17, the second throttle valve III-18, the second purifier III-19, the three-position four-port electromagnetic valve III-12, the pressure stabilizing valve III-16, the annular working chamber I-2, the gas sensor array I-1, the first throttle valve III-10 and the first flowmeter III-8, and finally, discharging the dry air outdoors lasting for 40s, and during this period, making the gas sensor array I-1 accurately restore to a reference state under the action of the dry air; wherein as the eighth two-position two-port electromagnetic valve III-15 is set to be off, whether the first two-position two-port electromagnetic valve III-1 to the fifth two-position two-port electromagnetic valve III-1 are off or on does not affect a calibration of the gas sensor array I-1.

5. The method for online detecting and analyzing a plurality of state parameters in fermentation and malodorous pollution processes by using an electronic nose instrument of gas sensitivity and gas chromatography of claim 1, wherein the "clean ambient air" is the kind of the outdoor air in where the electronic nose instrument is located by the dust removal, dehumidification and aseptic pretreatments; the clean ambient air is only used for the rough recovery of the gas sensor array I-1, flushing inner walls of the annular working chamber I-2 as well as related pipelines, and taking away the accumulated heat volume generated by the gas sensor array I-1; in two intervals of $[0, T_0-120s]$ and $[T_0-10s, T_0]$ in the single gas sampling period $T_0$, setting the three-position four-port electromagnetic valve III-12 to be "2", setting the sixth two-position two-port electromagnetic valve III-9 to be on, and setting the eighth two-position two-port electromagnetic valve III-15 to be off; and making the clean ambient air sequentially flow through, at a flow rate of 6,500 ml/min, the three-position four-port electromagnetic valve III-12, the pressure stabilizing valve III-16, the annular working chamber I-2, the gas sensor array I-1, the sixth two-position two-port electromagnetic valve III-9 and the first flowmeter III-8, and finally, discharging the clean ambient air outdoors and lasting for $T_0-110s$, and during this period, making the gas sensor array I-1 elementarily recover to a reference state under the role of the clean ambient air; wherein as the eighth two-position two-port electromagnetic valve III-15 is set to be off, whether the first two-position two-port electromagnetic valve III-1 to the fifth two-position two-port electromagnetic valve III-1 are off or on does not affect an rough recovery of the gas sensor array I-1.

6. The method for online detecting and analyzing a plurality of state parameters in fermentation and malodorous pollution processes by using an electronic nose instrument of gas sensitivity and gas chromatography of claim 1, wherein a size of a commercially available capillary gas chromatographic column II-1 is set to be a length 'L' times an inner diameter '$\phi$d' times a film thickness '$\delta$', namely L×$\phi$d×$\delta$=30m×$\phi$0.53 mm×0.25 μm, by default, and is located in a thermostatic box with a temperature of 250-300±0.1° C.; in the single gas sampling period $T_0$, making the capillary gas chromatographic column module II sequentially undergo three stages, i.e., a headspace sampling stage of the tested gas for 1s, a chromatographic separation stage of the tested gas for $T_0-16s$, and an emptying and purging stage for 15s; wherein $H_2$ is simultaneously used as a carrier gas and a fuel gas, and a dry air is used as a combustion-supporting gas; and an initial 1s of the single gas sampling period $T_0$ is the headspace sampling stage of the tested gas by the capillary gas chromatographic column module II, setting one two-position two-port electromagnetic valve III-k (k=1,2, . . . ,5) among the first two-position two-port electromagnetic valve III-1 to the fifth two-position two-port electromagnetic valve III-5 to be on, setting the two-position three-port electromagnetic valve III-11 to be "1", setting the seventh two-position two-port electromagnetic valve III-14 to be on, and setting the eighth two-position two-port electromagnetic valve III-15 to be off; and at this time, under the suction action of the second miniature vacuum pump III-13, making the tested gas at a monitoring point k sequentially flow through the two-position two-port electromagnetic valve III-k (k=1,2, . . . ,5) among the first two-position two-port electromagnetic valve III-1 to the fifth two-position two-port electromagnetic valve III-5, the seventh two-position two-port electromagnetic valve III-14, the two-position three-port electromagnetic valve III-11 and the fourth throttle valve III-24, and mixing with the carrier gas $H_2$ at the sampling inlet II-5 to flow into the capillary gas chromatographic column II-1 and last for 1s, wherein a sampling flow rate of the tested gas is 6 ml/min by default, a sampling duration is 1s by default, and an cumulative sampling amount is 0.1 ml by default.

7. The method for online detecting and analyzing a plurality of state parameters in fermentation and malodorous pollution processes by using an electronic nose instrument of gas sensitivity and gas chromatography of claim 1, wherein an interval of [1s, $T_0$–10s] in the single gas sampling period $T_0$ is the chromatographic separation stage of the capillary gas chromatographic column module II for the tested gas, and setting the two-position three-port electromagnetic valve III-11 to be "2", and setting the seventh two-position two-port electromagnetic valve III-14 to be off, so that tested gas from the monitoring point k cannot enter the gas chromatographic column module II for $T_0$–11s; and under the pushing action of the carrier gas $H_2$ with a certain pressure and a certain flow rate, separating, in the capillary gas chromatographic column II-1, the tested gas is injected into the sampling inlet II-5 of the gas chromatographic column module II, generating a perception response through the detector II-2, amplifying the perception response through the amplifier II-3, recording, by the recorder II-4, the perception response within an interval of [0, $T_0$–10s], i.e., a duration of $T_0$–10s of the chromatographic column II-1, and saving the perception response within the interval of [0, $T_0$–10s] in a temporary file of the computer control and analysis module IV.

8. The method for online detecting and analyzing a plurality of state parameters in fermentation and malodorous pollution processes by using an electronic nose instrument of gas sensitivity and gas chromatography of claim 1, wherein an interval of [$T_0$–10s, $T_0$] with a duration of 10s in the single gas sampling period $T_0$ is an emptying and purging stage of the capillary gas chromatographic column II-1, setting the one two-position two-port electromagnetic valve III-k in an originally on state among the first two-position two-port electromagnetic valve III-1 to the fifth two-position two-port electromagnetic valve III-5 to be off, and setting one of four two-position two-port electromagnetic valves in an originally off state among the first two-position two-port electromagnetic valve III-1 to the fifth two-position two-port electromagnetic valve III-5 to be on; setting the two-position three-port electromagnetic valve III-11 to be "2", setting the seventh two-position two-port electromagnetic valve III-14 to be on, setting the eighth two-position two-port electromagnetic valve III-15 to be off; assuming that the two-position two-port electromagnetic valve III-(~k) is on (k=1,2, . . . ,5), under the suction action of the second micro vacuum pump III-13, making a tested gas sequentially flow through, at a flow rate of 330 ml/min, the two-position two-port electromagnetic valve III-(~k), the seventh two-position two-port electromagnetic valve III-14 and the two-position three-port electromagnetic valve III-11, and finally, discharging the tested gas outdoors, so that gas residue from a monitoring point k in a current gas sampling period of a related pipeline is removed, and the pipeline is gradually filled with the tested gas from the monitoring point ~k to prepare a detection of next bio-fermentation process or malodorous pollution monitoring point in a next gas sampling period, and a detection duration is 10s; and an interval of [$T_0$–10s, $T_0$] of the single gas sampling period $T_0$ is still an information selection and analysis stage, selecting, by the computer control and analysis module IV, 48 pieces of perception information including a group of steady-state peak values $V_{gsi}(\tau)$, i=1, 2, . . . , 16, from a group of voltage response curves of the gas sensor array I-1 obtained in an interval of [$T_0$–75s, $T_0$–15s]; selecting 21 perception components including the first 10 maximum chromatographic peak values $V_{gcj}(\tau)$, j=1,2, . . . 10, from a chromatogram obtained in an interval of [0, $T_0$–10s], and being used as a basis of further doing an analysis on a bio-fermentation process or a malodorous pollution region by the electronic nose instrument; and performing, by the computer control and analysis module IV, a type identification of an odor and a quantitative prediction its overall intensity as well as the main concentration index values according to the current pattern vector $x(\tau)$ and the big odor data X.

9. The method for online detecting and analyzing a plurality of state parameters in fermentation and malodorous pollution processes by using an electronic nose instrument of gas sensitivity and gas chromatography of claim 1, wherein, in the single gas sampling period $T_0$, in a case where one bio-fermentation process or one malodorous pollution point is detected only, making the cyclical sampling period be $T=T_0$; in a case where k bio-fermentation processes or malodorous pollution points are simultaneously detected in sequence in the specified time stage, making the cyclical sampling period for one of a plurality of tested gas samples from the k bio-fermentation processes and/or malodorous pollution points be $T=k*T_0$; in a case where the one of the k bio-fermentation processes and/or malodorous pollution points exits from the current long-term circulation monitoring process, making the cyclical sampling period change of tested gas samples to be changed into $T=(k-1)*T_0$ from the original $T=k*T_0$; similarly, in the long-term circulation monitoring process, in a case where a new bio-fermentation processes or malodorous pollution point is added to the present long-term circulation detection process in the midway, making the cyclical sampling period of tested gas samples change into $T=(k+1)*T_0$, wherein a corresponding data recording period is changed from the moment while one bio-fermentation process or one malodorous pollution point exits or joins.

10. The method for online detecting and analyzing a plurality of state parameters in fermentation and malodorous pollution processes by using an electronic nose instrument of gas sensitivity and gas chromatography of claim 1, wherein in the single gas sampling period $T_0$, an interval of [$T_0$–10s, T0] is an information selection and analysis stage with a duration of 10s, performing, by the computer control and analysis module IV, information selection and analysis operations simultaneously on the gas sensor array module I and the capillary gas chromatographic column module II; selecting, by the computer control and analysis module IV, 3 components of perception information, i.e., a steady-state peak value $V_{gsi}(\tau)$, a corresponding peak time $t_{gsi}(\tau)$ and an area under the curve $A_{gsi}(\tau)$, from the $i^{th}$ voltage response curve of the gas sensor array I-1 obtained in an interval of [$T_0$–75s, $T_0$–15s] with a duration of 60s; selecting, by the computer control and analysis module IV, 21 perception response components, i.e., the first 10 maximum chromatographic peak values $V_{gcj}(\tau)$, the 10 retention time $t_{gcj}(\tau)$ corresponding to the first 10 maximum chromatographic peak values, and the 1 area $A_{gc}(\tau)$ under the semi-separation chromatogram curve from the capillary gas chromatographic column II-1 in an interval of [0, $T_0$–10s], i.e., a duration of 6s; and saving the 21 perception response components in a temporary file of the computer hard disk; and in the single gas sampling period $T_0$, in a case where the number of chromatographic peaks of the semi-separation chromatogram with a duration of $T_0$–10s is less than 10, or q<10, selecting, by the computer control and analysis module IV, the first q<10 maximum chromatographic peak values $h_{gcj}(\tau)$, the corresponding q<10 retention time values $t_{gcj}(\tau)$, and 1 area under the chromatogram curve $A_{gc}(\tau)$, all from the semi-separation chromatogram, and then performing a zero-filling operation to the insufficient peak values and the corresponding retention time values; wherein the obtained chromatogram perception information is $x_{gc}(\tau)=\{(h_{gc1}(\tau), h_{gc2}(t), \ldots, h_{gcq}(\tau), 0, \ldots, 0); (t_{gc1}(\tau), t_{gc2}(\tau), \ldots, t_{gcq}(\tau), 0, \ldots, 0); A_{gc}(\tau)\}$.

11. The method for online detecting and analyzing a plurality of state parameters in fermentation and malodorous pollution processes by using an electronic nose instrument of gas sensitivity and gas chromatography of claim 1, wherein a last 10s of the single gas sampling period $T_0$ is an information processing and analysis interval of $[T_0-10s, T_0]$, performing, by a modular machine learning model of the computer control and analysis module IV, a type identification of an odor and a quantitative prediction of its overall intensity as well as many concentration index values of main components on a bio-fermentation process and/or malodorous pollution point based on a recent time-series response matrix $X(\tau\text{-}q)$ given by a gas sensitivity and a gas chromatography, the method comprises: identifying a type of bio-fermentation process and a malodorous pollution point; performing a quantitative concentration estimation on cells, substrates and even bio-products in the plurality of bio-fermentation processes; for instance, performing a quantitative concentration estimation on such precursor substances as n-propanol and phenylacetic acid in different fermentation processes; and performing a quantitative concentration prediction on (8+1) kinds of malodorous pollutants specified by GB14554, wherein $\tau$ is a current time point, q is a recently elapsed time point, and $\tau$-q is a recent interval.

12. The method for online detecting and analyzing a plurality of state parameters in fermentation and malodorous pollution processes by using an electronic nose instrument of gas sensitivity and gas chromatography of claim 1, wherein the big odor data X further comprises: the gas sensitive/gas chromatographic data sensitized by an electronic nose instrument for a plurality of headspace vapors of simple compounds with a concentration of 0.1 ppm to 10000 ppm; offline detection data of a gas chromatographic, a mass spectrometric and a spectrophotometric instrument; professional laboratory olfactory data; and especially a plurality of simple compounds not only include such precursor substances as n-propanol, phenylacetic acid in the bio-fermentation processes; but also includes 8 malodorous compounds specified by GB14554; and the standard reference substance of odor concentration (OU) value, butanol, specified by the European standard EN13725.

13. The method for online detecting and analyzing a plurality of state parameters in fermentation and malodorous pollution processes by using an electronic nose instrument of gas sensitivity and gas chromatography of claim 1, wherein the machine learning model comprises a plurality of modular deep convolutional neural networks; the number of the modular single-output deep convolutional neural networks are equal to either the main predicted component number of fermentation liquors in the plurality of bio-fermentation processes plus the objective odor-type number detected, or the main concentration index number of malodorous pollutants plus the objective odor-type number, each for one; one single-output deep convolutional neural network in the plurality of modular single-output deep convolutional neural networks comprises 1 input layer, 3 convolutional layers, 2 down-sampling layers and 1 output unit, and activation functions in each convolutional layer, each down-sampling layer and the output layer are all a Sigmoid correction activation function $f(\varphi)=3(1+\exp(-\varphi/3))-1$; in the learning stage, adopting, by the each single-output deep convolutional neural network, an offline layer-wise error back-propagation algorithm to mainly learn the big odor data X with labels and/or known components; setting a scan window in each convolutional layer to be 55, and setting an overlapping scan step length to be 1; making 6 single-type kernels, a sine, a cosine, a polynomial, a Gaussian, a Sigmoid, a wavelet and a Laplace kernel to form a group of combined convolution kernels; setting a scan window in each down-sampling layer to be 2×2, setting a non-overlapping scan step length to be 2, and extracting such 3 features as a maximum, a mean and a mean-square-error value; and in the decision-making stage, performing, by n single-output deep convolutional neural network models, an odor type identification, and an intensity estimation and prediction of their intensities and main component concentrations one by one at a current time point t and coming $\tau$+1, $\tau$+2 and $\tau$+3, according to a current gas sensitive/gas chromatographic response vector $x(\tau)$ and a recently occurred time-series response matrix $X(\tau\text{-}q)$.

14. The method for online detecting and analyzing a plurality of state parameters in fermentation and malodorous pollution processes by using an electronic nose instrument of gas sensitivity and gas chromatography of claim 1, wherein performing, by the electronic nose instrument, a long-term online circulation detection and an online analysis prediction of a plurality of bio-fermentation processes/malodorous pollution points comprises:

(1) power-on operation: performing a preheating operation in the electronic nose instrument for 30 min;
setting the single gas sampling period $T_0$ in a screen menu as a default value $T_0$-8 min, and setting a cyclical gas sampling period for 5 monitoring points to be $T=5T_0$;
setting the three-position four-port electromagnetic valve III-12 to be "2", setting the sixth two-position two-port electromagnetic valve III-9 to be on and the eighth two-position two-port electromagnetic valve III-15 to be off, under the suction action of the first miniature vacuum pump III-7, making clean ambient air to sequentially flow through, at a flow rate of 6,500 ml/min, the three-position four-port electromagnetic valve III-12, the pressure stabilizing valve III-16, the annular working chamber I-2, the gas sensor array I-1, the sixth two-position two-port electromagnetic valve III-9 and the first flowmeter III-8, and finally, discharging the clean ambient air to outdoor, and therefore, making the annular working chamber I-2 reach a constant internal temperature of 55±0.1° C.; and
setting the two-position three-port electromagnetic valve III-11 to be "2", and setting the seventh two-position two-port electromagnetic valve III-14 to be off, under the pushing role of the carrier gas $H_2$, making the capillary gas chromatographic column II-1 gradually recover to a reference state, and making the chromatographic column box reach a constant internal temperature of 250±0.1° C.;

(2) beginning a cyclical gas sampling period:
clicking an option with "monitoring point k on" in a screen menu of the display IV-5, wherein k=1, 2, . . . , 5, performing, by the electronic nose instrument, a continuous and cyclical detection until the operator clicks an option with "monitoring point k off"; in a process that the electronic nose instrument performs a cyclical detection on the 5 monitoring points in order, automatically generating, by the computer control and analysis module IV, 5 text files respectively to save the sensitive response data of the gas sensor array I-1 and the capillary gas chromatographic column module II to the tested gases at the 5 monitoring points;

(3) beginning the single gas sampling period at a monitoring point k among the 5 monitoring points: taking a default period value $T_0$=8 min as an example:

(3.1) for the gas sensor array module I: undergoing the following six gas sampling stages in order, i.e., (i) an rough recovery stage for 360s, (ii) an accurate calibration stage for 40s, (iii) a balance stage for 5s, (iv) a headspace sampling stage for 60s, (v) a transition stage for 5s, and (vi) a cleaning and rough recovery stage for 10s, (3.1a) the rough recovery stage from 0s to the 360th sec of the single gas sampling period $T_0$, setting the three-position four-port electromagnetic valve III-12 to be "2", setting the sixth two-position two-port electromagnetic valve III-9 to be on, and setting the eighth two-position two-port electromagnetic valve III-15 to be off; and under the suction action of the first miniature vacuum pump III-7, making the clean ambient air flow through, at a flow rate of 6,500 ml/min, the three-position four-port electromagnetic valve III-12, the pressure stabilizing valve III-16, the annular working chamber I-2, the gas sensor array I-1, the sixth two-position two-port electromagnetic valve III-9 and the first flowmeter III-8 in order, and finally, discharging the clean ambient air to outdoor; and therefore, making the gas sensor array I-1 initially recover to a reference state;

(3.1b) for the accurate calibration stage from the $360^{th}$ sec to the $400^{th}$ sec of the single gas sampling period $T_0$, setting the three-position four-port electromagnetic valve III-12 to be "1", setting the sixth two-position two-port electromagnetic valve III-9 to be off, setting the seventh two-position two-port electromagnetic valve III-14 to be off, and setting the eighth two-position two-port electromagnetic valve III-15 to be off; and under the suction action of the first miniature vacuum pump III-7, making dry air flow through, at a flow rate of 1,000 ml/min, the first pressure reducing valve III-17, the second throttle valve III-18, the second purifier III-19, the three-position four-port electromagnetic valve III-12, the pressure stabilizing valve III-16, the annular working chamber I-2, the gas sensor array I-1 in the annular working chamber I-2, the first throttle valve III-10 and the first flowmeter III-8 in order, and finally, discharging the dry air to outdoor and lasting for 40s, and therefore, making the gas sensor array I-1 accurately recover to a reference state;

(3.1c) for the balance stage from the $400^{th}$ sec to the $405^{th}$ sec of the single gas sampling period $T_0$, setting the three-position four-port electromagnetic valve III-12 to be "0", setting the sixth two-position two-port electromagnetic valve III-9 to be off, and setting the eighth two-position two-port electromagnetic valve III-15 to be off, so that no gas flows in the annular working chamber I-2 for 5s;

(3.1d) for the headspace sampling stage from the $405^{th}$ sec to the $465^{th}$ sec of the single gas sampling period $T_0$, setting the two-position two-port electromagnetic valve III-k (k=1,2, . . . ,5) among the first two-position two-port electromagnetic valve III-1 to the fifth two-position two-port electromagnetic valve III-5 to be on, setting the three-position four-port electromagnetic valve III-12 to be "0", setting the sixth two-position two-port electromagnetic valve III-9 to be off, setting the seventh two-position two-port electromagnetic valve III-14 to be off, and setting the eighth two-position two-port electromagnetic valve III-15 to be on, wherein k=1, 2, . . . , 5; and under the suction action of the first miniature vacuum pump III-7, making the tested gas at a monitoring point flow through, at a flow rate of 1,000 ml/min, the two-position two-port electromagnetic valve III-k (k=1,2, . . . ,5), the eighth two-position two-port electromagnetic valve III-15, the pressure stabilizing valve III-16, the annular working chamber I-2 and the gas sensor array I-1, the first throttle valve III-10 and the first flowmeter III-8 in order, and finally, discharging the tested gas to outdoor and lasting for 60s, and therefore, generating, by the gas sensor array I-1, a sensitive response, and saving the sensitive response in a temporary file corresponding to the computer control and analysis module IV;

(3.1e) for the transition stage from the $465^{th}$ sec to the $470^{th}$ sec of the single gas sampling period $T_0$, setting the three-position four-port electromagnetic valve III-12 to be "2", setting the eighth two-position two-port electromagnetic valve III-15 to be off, setting the sixth two-position two-port electromagnetic valve III-9 to be off, and setting the seventh two-position two-port electromagnetic valve III-14 to be off; and under the suction action of the first miniature vacuum pump III-7, making the clean ambient air flow through, at a flow rate of 1,000 ml/min, the three-position four-port electromagnetic valve III-12, the pressure stabilizing valve III-16, the annular working chamber I-2 and the gas sensor array I-1, the sixth two-position two-port electromagnetic valve III-9 and the first flowmeter III-8 in order, and finally, discharging the clean ambient air to outdoor;

(3.1f) for the cleaning and rough recovery stage from the $470^{th}$ sec to the $480^{th}$ sec of the single gas sampling period $T_0$, compared with the "transition stage", making the positions of the rest valves be the same except that the sixth two-position two-way electromagnetic valve III-9 is changed from "off" to "on"; making the flow rate of the clean ambient air thus change from "1,000 ml/min" to "6,500 ml/min"; and making a valve position and a working state of the stage be completely the same and match with a valve position and a working state of a "rough recovery" stage of a next gas sampling period;

(3.2) for a capillary gas chromatographic column II module, sequentially undergoing (i) a headspace sampling stage for 1s, (ii) a chromatographic separation stage for 469s and (iii) an emptying and cleaning stage for 10s;

(3.2 a) for the headspace sampling stage from 0s to the $1^{st}$ sec of the single gas sampling period $T_0$, setting one two-position two-port electromagnetic valve III-k (k=1,2, . . . ,5) among the first two-position two-port electromagnetic valve III-1 to the fifth two-position two-port electromagnetic valve III-5 to be on, setting the two-position three-port electromagnetic valve III-11 to be "1", setting the seventh two-position two-port electromagnetic valve III-14 to be on, and setting the eighth two-position two-port electromagnetic valve III-15 to be off; and under the suction action of the second miniature vacuum pump III-13, making the tested gas at a monitoring point k flow through the $k^{th}$ two-position two-port electromagnetic valve III-k (k=1,2, . . . ,5), the seventh two-position two-port electromagnetic valve III-14, the two-position three-port electromagnetic valve III-11 and the fourth throttle valve III-24 in order, and mixing with the carrier gas $H_2$ at the sampling inlet II-5 to flow into the capillary gas chromatographic column II-1 for 1s;

(3.2 b) for the chromatographic separation stage from the $1^{st}$ sec to the 470th sec of the single gas sampling period $T_0$, setting the two-position three-port electromagnetic valve III-11 to be "2", and setting the seventh two-position two-port electromagnetic valve III-14 to be off; and under the pushing role of carrier gas $H_2$ with a certain pressure and flow, separating the tested gas in the capillary gas chromatographic column II-1, generating a perception response through the detector II-2, amplifying the perception response through the amplifier II-3, recording, by the recorder II-4, the perception response at a duration of 470s within an interval of [0, 470s] to form a semi-separation chromatographic peak graph; and saving the semi-separation chromatographic peak graph in a temporary file corresponding to the computer control and analysis module IV;

(3.3) information selection and analysis operation, in a time interval from the $470^{th}$ sec to the $480^{th}$ sec of the single gas sampling period $T_0$, selecting, by the computer control and analysis module IV, 3 pieces of sensitive information, i.e., a steady-state peak value $V_{gsi}(\tau)$, a corresponding peak time $t_{gsi}(\tau)$, and an area under the whole curve $A_{gsi}(\tau)$ from a single voltage response curve which is obtained by each gas sensor in an interval of [405s, 465s] and lasts for 60s, to obtain 16*3-48 pieces of sensitive information by the gas sensor array I-1 comprising 16 gas sensors; simultaneously selecting, by the computer control and analysis module IV, first 10 maximum chromatographic peak values $v_{gcj}(\tau)$, 10 corresponding retention time values $t_{gcj}(\tau)$, and an area under a total chromatogram curve $A_{gc}(\tau)$ from the semi-separation chromatogram with a duration of 470s by the capillary gas chromatographic column module II, to obtain 21 pieces of perception information; obtaining, by the computer control and analysis module IV, 1 response vector $x(\tau) \in R^{69}$ with 69 dimensions from the sensitive information of the gas sensor array module I and the capillary chromatography column module II in the signal gas sampling period $T_0$; and performing, by a machine learning model, an odor type identification and an intensity and main component quantitative prediction based on the sensitive vector $x(\tau)$ and the big odor data X, displaying, by the display, a monitoring and prediction result, and transmitting, through an Internet network, the monitoring and prediction result to a central control room and a plurality of fixed/mobile terminals;

(3.4) ending the current monitoring point k and beginning a next monitoring point;

setting the $k^{th}$ two-position two-port electromagnetic valve III-k (k=1,2, ... ,5) among the first two-position two-port electromagnetic valve III-1 to the fifth two-position two-port electromagnetic valve III-5 to be from 'on' to 'off', and setting the two-position two-port electromagnetic valve corresponding to a next monitoring point among the first two-position two-port electromagnetic valve III-1 to the fifth two-position two-port electromagnetic valve III-5 to be on;

(4) repeating the steps (3.1)~(3.4), and realizing, by the electronic nose instrument, online cyclical detection, identification and quantitative prediction of odor intensity and a plurality of concentration index values of the tested gases at the 1~5 monitoring points.

\* \* \* \* \*